(12) United States Patent
Yamaguchi

(10) Patent No.: US 11,439,477 B2
(45) Date of Patent: Sep. 13, 2022

(54) MEDICAL OBSERVATION SYSTEM

(71) Applicant: SONY OLYMPUS MEDICAL SOLUTIONS INC., Tokyo (JP)

(72) Inventor: Kazuhiro Yamaguchi, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 139 days.

(21) Appl. No.: 16/282,345

(22) Filed: Feb. 22, 2019

(65) Prior Publication Data

US 2019/0290384 A1 Sep. 26, 2019

(30) Foreign Application Priority Data

Mar. 23, 2018 (JP) .............................. JP2018-057220

(51) Int. Cl.
| | | |
|---|---|---|
| *A61B 90/20* | (2016.01) | |
| *G02B 21/00* | (2006.01) | |
| *A61B 90/30* | (2016.01) | |
| *A61B 90/00* | (2016.01) | |
| *A61B 90/50* | (2016.01) | |

(52) U.S. Cl.
CPC .............. *A61B 90/20* (2016.02); *A61B 90/30* (2016.02); *G02B 21/0012* (2013.01); *A61B 90/36* (2016.02); *A61B 90/50* (2016.02)

(58) Field of Classification Search
CPC .... G02B 21/0012; G02B 21/18; G02B 21/36; G02B 27/34; G02B 27/20; A61B 90/30; A61B 90/20; A61B 19/00; A61B 90/36; A61B 90/50; A61B 90/25; A61B 2090/306; A61B 2090/508; A61B 2090/309; A61B 2034/204
See application file for complete search history.

(56) References Cited

U.S. PATENT DOCUMENTS

| | | | | |
|---|---|---|---|---|
| 8,477,416 B2* | 7/2013 | Nakamura | ......... | G02B 21/0012 359/376 |
| 2009/0326553 A1* | 12/2009 | Mustufa | ................ | A61B 34/30 606/130 |
| 2014/0015957 A1* | 1/2014 | Fujikawa | ................ | H04N 7/18 348/95 |
| 2017/0086940 A1* | 3/2017 | Nakamura | ............. | A61B 10/00 |
| 2018/0136448 A1* | 5/2018 | Cramb | ................ | G02B 21/361 |

FOREIGN PATENT DOCUMENTS

| | | |
|---|---|---|
| JP | 2001-299695 | 10/2001 |
| JP | 2005-161086 | 6/2005 |
| JP | 2017037238 A | 2/2017 |
| WO | WO-2015198578 A1 | 12/2015 |

* cited by examiner

*Primary Examiner* — Balram T Parbadia
*Assistant Examiner* — Gabriel A Sanz
(74) *Attorney, Agent, or Firm* — Xsensus LLP

(57) ABSTRACT

A disclosed medical observation system includes a capturing unit operable to capture an image of an observation target; and a light projection unit operable to project light on the observation target, outside a capturing area that is captured by the capturing unit and in a periphery of the capturing area, the light enabling recognition of a capturing state of the capturing unit.

20 Claims, 24 Drawing Sheets

MEDICAL OBSERVATION SYSTEM

CROSS-REFERENCE TO RELATED APPLICATION(S)

The present application claims priority to and incorporates by reference the entire contents of Japanese Patent Application No. 2018-057220 filed in Japan on Mar. 23, 2018.

BACKGROUND

The present disclosure relates to a medical observation system.

For example, there is known a surgical microscope for observing a very small part of a brain, a heart or the like of a patient, which is an observation target, at the time of performing a surgery on the very small part. Furthermore, there is known a surgical microscope having a capturing unit installed at a distal end of a movable arm, according to which a capturing area to be captured by the capturing unit may be easily moved (for example, see Japanese Laid-open Patent Publications No. 2005-161086 A and No. 2001-299695 A).

SUMMARY

An operator such as a surgeon moves the capturing area while observing a display device on which an image captured by the capturing unit is displayed. Accordingly, it has been rather hard for an operator to intuitively recognize the capturing area.

The present disclosure has been made in view of the above, and is directed to a medical observation system.

According to a first aspect of the present disclosure, a medical observation system is provided which includes a capturing unit operable to capture an image of an observation target; and a light projection unit operable to project light on the observation target, outside a capturing area that is captured by the capturing unit and in a periphery of the capturing area, the light enabling recognition of a capturing state of the capturing unit.

According to a second aspect of the present disclosure, a medical observation system is provided which includes a capturing unit operable to capture an image of an observation target; and a light emitting unit operable to emit first illumination light in a capturing direction of the capturing unit, wherein the light emitting unit radiates second illumination light on the observation target, outside a capturing area that is captured by the capturing unit and in a periphery of the capturing area, the second illumination light enabling recognition of a capturing state of the capturing unit.

The above and other objects, features, advantages and technical and industrial significance of this disclosure will be better understood by reading the following detailed description of presently preferred embodiments of the disclosure, when considered in connection with the accompanying drawings.

DETAILED DESCRIPTION

Hereinafter, embodiments of a medical observation system according to the present disclosure will be described with reference to the drawings. However, the present disclosure is not limited to these embodiments. The present disclosure may be generally applied to a medical observation system provided with a capturing unit.

In the description of the drawings, same or corresponding elements are denoted by a same reference sign as appropriate. Moreover, it should be noted that the drawings are schematic, and do not necessarily represent actual dimensional relationships, ratios and the like of the elements. Furthermore, dimensional relationships, ratios and the like may be different between the drawings.

First Embodiment

Schematic Configuration of Medical Observation System

Figure 1:
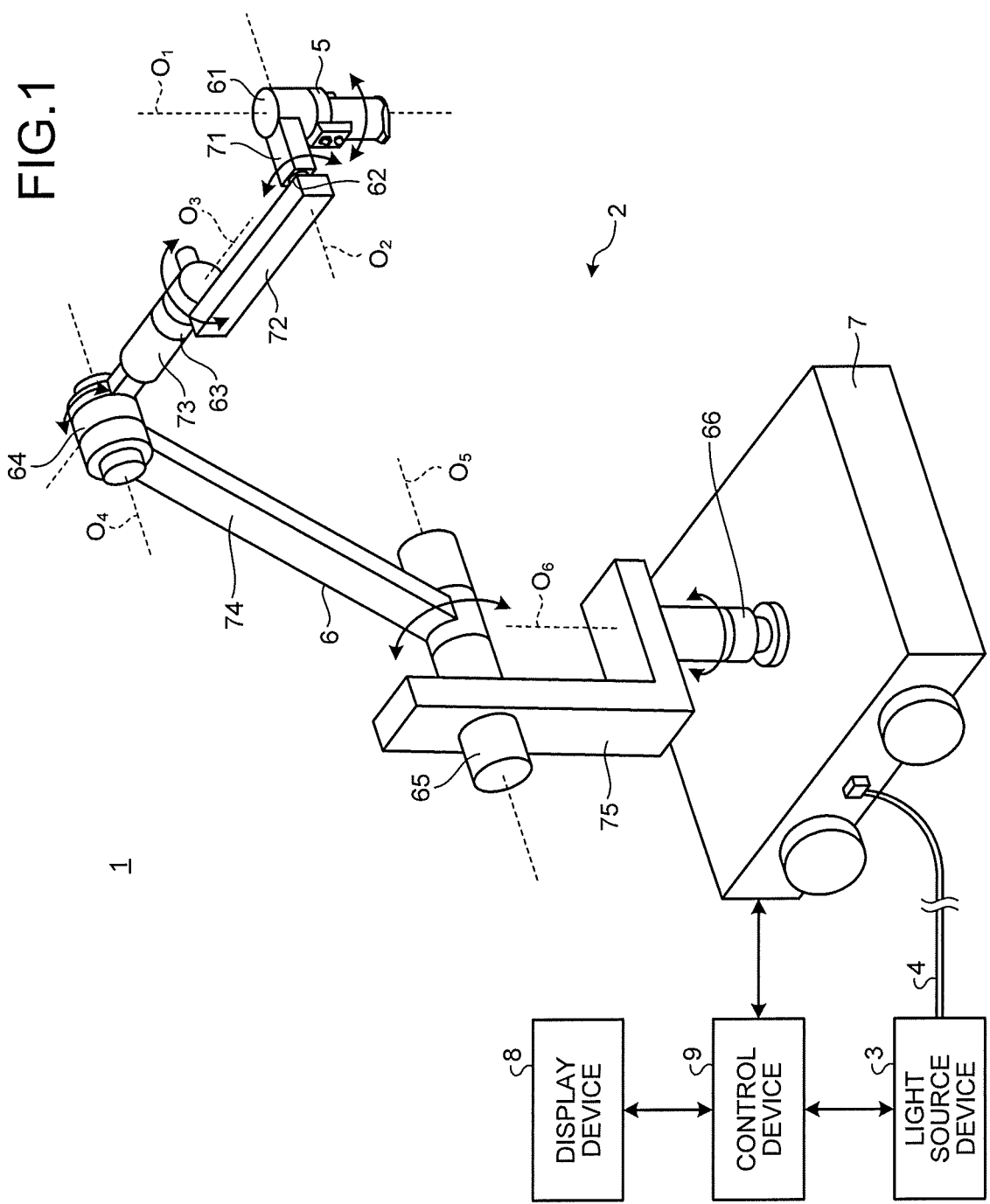
FIG. 1 is a diagram illustrating an overall configuration of a medical observation system according to a first embodiment.

FIG. 1 is a diagram illustrating an overall configuration of a medical observation system according to a first embodiment. A medical observation system 1 illustrated in FIG. 1 includes a medical observation device 2 serving as a microscope for enlarging and observing a very small part of an observation target, a light source device 3 for supplying illumination light to the observation device 2 through a light guide 4 configured of an optical fiber or the like, a display device 8 for displaying an image that is captured by the observation device 2, and a control device 9 for integrally controlling operation of the medical observation system 1.

Schematic Configuration of Observation Device

First, a schematic configuration of the observation device 2 will be described.

The observation device 2 includes a microscope unit 5 for observing a very small part of an observation target, a support section 6 that is connected to a proximal end portion of the microscope unit 5 and that is for rotatably supporting the microscope unit 5, and a base section 7 that is for rotatably holding a proximal end portion of the support section 6 and that is movable on a floor surface.

Figure 2:
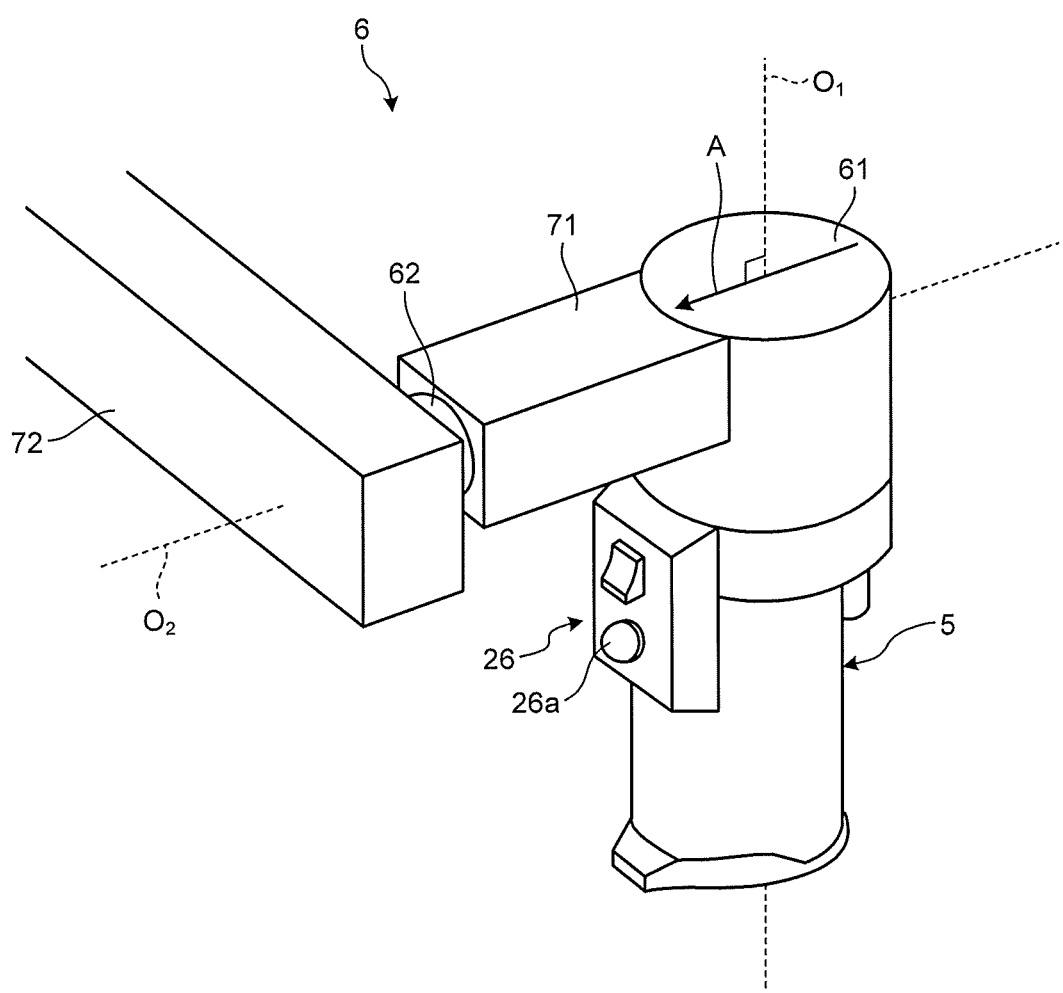
FIG. 2 is an enlarged perspective view illustrating a configuration of and around a microscope unit according to the first embodiment.

FIG. 2 is an enlarged perspective view illustrating a configuration of the microscope unit 5 and peripheral parts around the microscope unit 5 according to the first embodiment. The microscope unit 5 has a circular cylindrical shape, and includes, in its inside, an optical system having a zoom function and a focus function, an image sensor (not illustrated) for receiving a subject image formed by the optical system and for generating an image signal by performing photoelectric conversion, and a light emitting unit (not illustrated) for radiating illumination light on an observation target. Various switches including an arm operation switch 26a, which constitutes a first input unit 26 for receiving input of an operation instruction for the observation device 2, are provided on a side surface of the microscope unit 5. When an operator presses the arm operation switch 26a, fixation of the support section 6 is released, and the microscope unit 5 is placed in a movable state. In other words, the operator may move a capturing area by pressing the arm operation switch 26a. Incidentally, a direction A, of the microscope unit 5, in which the arm operation switch 26a is installed is an up direction of a capturing unit 21. A correspondence relationship between the up direction of the capturing unit 21 and the capturing area will be described later. A cover glass (not illustrated) is provided on an aperture surface at a lower end portion of the microscope unit 5. The cover glass protects the optical system and the like inside the microscope unit 5. An operator such as a surgeon operates various switches while holding the microscope unit 5, and moves the microscope unit 5, changes an angle of the microscope unit 5, changes a mode of the observation device 2, or performs a zoom or focus operation, for example. Accordingly, the operator may intuitively grasp a direction of an optical axis of the optical system or a center direction of an imaging visual field of the microscope unit 5, and may easily move the microscope unit 5 to a desired position. Additionally, the shape of the microscope unit 5 is not limited to a circular cylindrical shape, and may be a polygonal cylindrical shape, for example.

Referring back to FIG. 1, the configuration of the observation device 2 will be described.

In the support section 6, a first joint portion 61, a first arm portion 71, a second joint portion 62, a second arm portion 72, a third joint portion 63, a third arm portion 73, a fourth joint portion 64, a fourth arm portion 74, a fifth joint portion 65, a fifth arm portion 75, and a sixth joint portion 66 are coupled in this order from a distal end side (microscope unit 5 side).

The first joint portion 61 holds at a distal end thereof the microscope unit 5 rotatably around a first axis $O_1$, which coincides with an optical axis of the microscope unit 5. A proximal end side of the first joint portion 61 is fixed to a distal end portion of the first arm portion 71 and thus held by the first arm portion 71.

The second joint portion 62 holds at a distal end thereof the first arm portion 71, rotatably around a second axis $O_2$, which is perpendicular to the first axis $O_4$. A proximal end side of the second joint portion 62 is held by the second arm portion 72. In the same manner, the third joint portion 63 to the sixth joint portion 66 rotatably hold the second arm portion 72 to the fourth arm portion 74 on respective distal end sides, and proximal end sides of the third joint portion 63 to the sixth joint portion 66 are fixed to respective distal end portions of the third arm portion 73 to the fifth arm portion 75 and thus held by the third arm portion 73 to the fifth arm portion 75, respectively.

The sixth joint portion 66 rotatably holds the fifth arm portion 75 at the distal end side, and the proximal end side of the sixth joint portion 66 is held fixed to the base section 7 and thus held by the base section 7.

The second arm portion 72 to the fifth arm portion 75 are rotatable with a third axis $O_3$ to a sixth axis $O_6$ as rotation axes, respectively. Each of the fourth axis $O_4$ and the fifth axis $O_5$ is parallel to the second axis $O_2$. The third axis $O_3$ and the fourth axis $O_4$ are perpendicular to each other, and the fifth axis $O_5$ and the sixth axis $O_6$ are perpendicular to each other.

The first joint portion 61 to the sixth joint portion 66 include corresponding angle sensors (not illustrated) serving as detection units and corresponding electromagnetic brakes (not illustrated) for controlling rotation of corresponding ones of the microscope unit 5 and the first arm portion 71 to the fifth arm portion 75 at the respective distal ends. The electromagnetic brakes are released when the arm operation switch 26a of the first input unit 26 of the microscope unit 5 is pressed. When the electromagnetic brakes are released, the microscope unit 5 and the first arm portion 71 to the fifth arm portion 75 become rotatable with respect to the first joint portion 61 to the sixth joint portion 66, respectively. In the following, a state where the microscope unit 5 and the first arm portion 71 to the fifth arm portion 75 are rotatable with respect to the first joint portion 61 to the sixth joint portion 66, respectively, will be referred to as "all free mode". Incidentally, other means such as an air brake may be used instead of the electromagnetic brake.

The first joint portion 61 to the sixth joint portion 66 are provided with actuators (not illustrated) for assisting rotation of the corresponding ones of the microscope unit 5 and the first arm portion 71 to the fifth arm portion 75. Furthermore, various sensors (not illustrated) serving as detection units for detecting at least one of a position, a speed, an acceleration, a rotation angle, a rotational speed, a rotational acceleration, or generated torque of respective joint portions are provided at the first joint portion 61 to the sixth joint portion 66.

The support section 6 configured above allows the microscope unit 5 to move in a total of six degrees of freedom, namely, three translational degrees of freedom and three rotational degrees of freedom. Incidentally, the support section 6 according to the first embodiment does not necessarily have all the actuators, and modifications may be made as appropriate. For example, one or some of the first arm portion 71 to the fifth arm portion 75 of the support section 6 are provided with the actuator.

The light source device 3 supplies illumination light to the observation device 2 through the light guide 4, under control of the control device 9. The light source device 3 is configured by using a discharge lamp such as a xenon lamp or a metal halide lamp, a solid-state light emitting device such as a light emitting diode (LED) or a laser diode (LD), or a light emitting member such as a laser light source or a halogen lamp.

The display device 8 displays a display image (video signal) that is generated by the control device 9, and various pieces of information about the medical observation system. The display device 8 is configured using liquid crystal or electro luminescence (EL), for example. Furthermore, a monitor size of the display device 8 is 31 inches or more, or more preferably, 55 inches or more. In the first embodiment, the monitor size of the display device 8 is assumed to be 31 inches or more, but this is not restrictive, and any monitor size is allowed as long as it is possible to display an image with a resolution of 2 megapixels (such as a so-called 2K resolution of 1920×1080 pixels) or more, or more preferably, a resolution of 8 megapixels (such as a so-called 4K resolution of 3840×2160 pixels) or more, and even more preferably, a resolution of 32 megapixels (such as a so-called 8K resolution of 7680×4320 pixels) or more. The display device 8 may, of course, be a monitor capable of displaying a 3D image.

The control device 9 comprehensively controls each unit of the medical observation system 1. The control device 9 is implemented by using a general-purpose processor such as a central processing unit (CPU), or a dedicated processor such as various calculation circuits for achieving specific functions, such as an application specific integrated circuit (ASIC). The control device 9 may be implemented by a field programmable gate array (FPGA; not illustrated), which is a type of programmable integrated circuit. The control device 9 controls each unit of the medical observation system 1 according to a command (instruction), recorded in a recording unit 93 described later, for controlling each unit. Incidentally, when the FPGA is used, a memory storing configuration data may be provided, and the FPGA, which is a programmable integrated circuit, may be configured by the configuration data read from the memory. A detailed configuration of the control device 9 will be described later.

Functional Configuration of Medical Observation System

Figure 3:
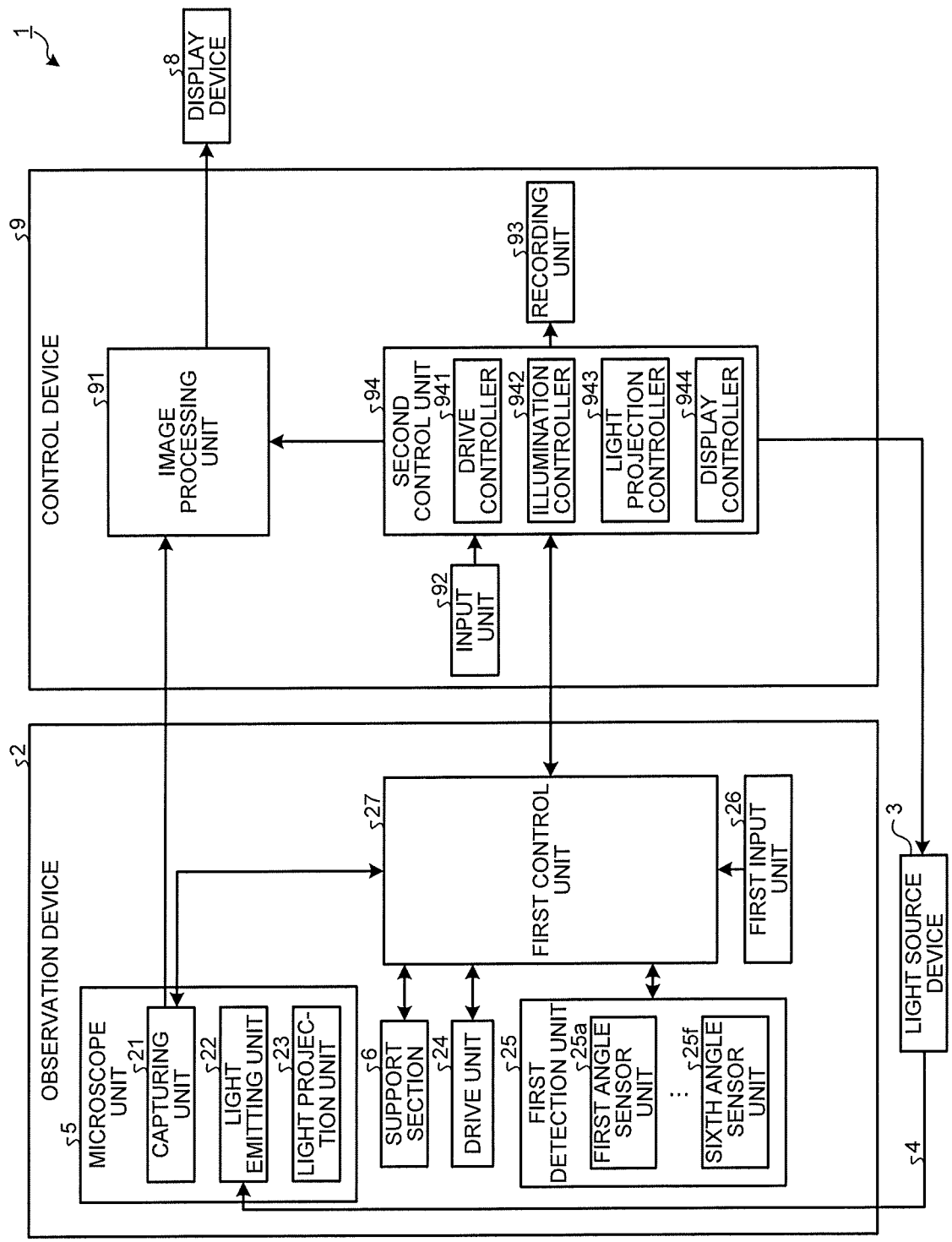
FIG. 3 is a block diagram illustrating a functional configuration of the medical observation system according to the first embodiment.

Next, a functional configuration of the medical observation system 1 described above will be described. FIG. 3 is a block diagram illustrating a functional configuration of the medical observation system according to the first embodiment.

Configuration of Observation Device

First, a functional configuration of the observation device 2 will be described.

The observation device 2 includes the microscope unit 5, the support section 6, a drive unit 24, a first detection unit 25, the first input unit 26, and a first control unit 27.

The microscope unit 5 includes the capturing unit 21 for generating an image signal by enlarging and capturing an image of an observation target, which is a subject, a light emitting unit 22 for radiating illumination light, supplied from the light source device 3, toward the observation target, and a light projection unit 23 for projecting light on the observation target.

The capturing unit 21 includes the optical system including the zoom and focus functions, and the image sensor for receiving an image of the observation target formed by the optical system and for generating an image signal by performing photoelectric conversion. The image sensor is configured by using a charge coupled device (CCD) or a complementary metal oxide semiconductor (CMOS). The image signal generated by the capturing unit 21 is transmitted to the control device 9 through a transmission cable 10. Incidentally, the image signal generated by the capturing unit 21 may be transmitted to the control device 9 as an optical signal after being subjected to Optical/Electrical (E/O) conversion. Additionally, it is sufficient that the capturing unit 21 has a resolution of 2 megapixels (such as a so-called 2K resolution of 1920×1080 pixels) or more, or more preferably, a resolution of 8 megapixels (such as a so-called 4K resolution of 3840×2160 pixels) or more, and even more preferably, a resolution of 32 megapixels (such as a so-called 8K resolution of 7680×4320 pixels) or more. Furthermore, the capturing unit 21 may generate a 3D image signal by generating two image signals by two image sensors with a predetermined parallax.

The light emitting unit 22 includes an illumination optical system configured by using one or a plurality of lenses. The light emitting unit 22 radiates the illumination light supplied from the light source device 3 through the light guide 4, in a same direction as a capturing direction of the capturing unit 21. Incidentally, when the microscope unit 5 is provided with an LED, a laser light source, or the like, light transmission to the light emitting unit 22 through the light guide or the like may be omitted.

As in FIGS. 1 and 2 described above, the support section 6 rotatably supports the microscope unit 5. The support section 6 configured above allows the microscope unit 5 to move in a total of six degrees of freedom, namely, three translational degrees of freedom and three rotational degrees of freedom.

The light projection unit 23 projects light on a region of the observation target, the region being outside a capturing area (image-capturing area) to be captured by the capturing unit 21 and in a periphery of the capturing area. The light enables recognition of a capturing state of the capturing unit 21. Specifically, the light projection unit 23 projects a pattern (patterned illumination) for enabling recognition of the capturing area, in relation to the capturing state of the capturing unit 21. The pattern is a frame surrounding the capturing area or a marker indicating a predetermined position of the capturing area, for example but is not limited to any particular pattern, as long as the capturing area may be recognized. The light projection unit 23 is configured by using a solid-state light emitting device such as a laser diode (LD), a laser light source, a discharge lamp such as a xenon lamp or a metal halide lamp, or a light emitting member such as an LED, for example. Incidentally, a laser light source, an LED or the like may be provided at the light source device 3, as the light projection unit, and transmission to the microscope unit 5 may be performed through the light guide 4. The light projection unit 23 may constantly project light on the observation target, or may project light according to an instruction from an operator, such as an input to the first input unit 26 or an input unit 92. For example, the light projection unit 23 may project light while the first input unit 26 is receiving input. Specifically, the light projection unit 23 may project light while the arm operation switch 26a of the first input unit 26 is being pressed. In the present specification, a periphery of a capturing area B is an area of about 50 mm from an outer circumference of the capturing area B, for example, but this is not restrictive. Furthermore, in the present specification, the capturing state is a state of the capturing unit 21, including a size of the capturing area, a direction of the capturing area, and the like. The direction of the capturing area is a correspondence relationship between a direction of an image that is displayed on the display device 8 and a direction of the capturing unit 21.

The drive unit 24 includes the electromagnetic brake and the actuator that are provided to each of the first joint portion 61 to the sixth joint portion 66. The electromagnetic brake is released in response to a release instruction that is input to the first input unit 26 at a time of all free mode operation. The actuator operates according to a control signal that is transmitted from the control device 9 described later, according to a state detection result from the first detection unit 25.

The first detection unit 25 sequentially detects state information of the observation device 2. The state information of the observation device 2 includes a position of the capturing unit 21, information about focus and zoom, information about at least one of a position, a speed, an acceleration, a rotation angle, a rotational speed, a rotational acceleration, or generated torque of each of the first joint portion 61 to the sixth joint portion 66, information about at least one of a position, a speed, and an acceleration of each of the first arm portion 71 to the fifth arm portion 75, and information about operation, such as an electric visual field movement mode or the all free mode. The first detection unit 25 includes various sensors for detecting these pieces of information. Specifically, the first detection unit 25 includes a first angle sensor unit 25a to a sixth angle sensor unit 25f for detecting angles of the first arm portion 71 to the fifth arm portion (the first axis $O_1$ to the sixth axis $O_6$), respectively, with respect to a reference direction. The reference direction here is a gravity direction (vertically downward direction) when the observation device 2 (the first arm portion 71 to the fifth arm portion 75) is installed on the floor. That is, in the first embodiment, a description is given assuming that the reference direction is 0 degrees. It is needless to say that the reference direction changes depending on an installation position of the observation device 2 (the first arm portion 71 to the fifth arm portion 75). For example, when the observation device 2 (the first arm portion 71 to the fifth arm portion 75) is installed suspended from a ceiling, the reference direction is different by 180 degrees from the case of floor installation. When the observation device 2 (the first arm portion 71 to the fifth arm portion 75) is installed fixed to a wall (fixed on a vertical wall), the reference direction is different by 90 degrees from the case of floor installation. Incidentally, the first angle sensor unit 25a may be omitted when the direction of the first axis $O_1$ to be detected by the first angle sensor unit 25a and the capturing direction of the capturing unit 21 are the same.

The direction A (FIG. 2), which is perpendicular to the first axis $O_1$ and in which the arm operation switch 26a of the microscope unit 5 is installed, is the up direction of the capturing unit 21. The up direction of the capturing unit 21 corresponds to an up direction of a screen that is shown on the display device 8. The first detection unit 25 detects an angle formed by the up direction of the capturing unit 21 and the vertically downward direction, as an angle formed by the reference direction and the second axis $O_2$. Furthermore, the first detection unit 25 may detect the gravity direction by providing an accelerometer at the microscope unit 5, and may detect an angle formed by the up direction of the capturing unit 21 and the vertically downward direction.

An XY operation mode included in the electric visual field movement mode is an operation mode in which the imaging visual field of the capturing unit 21 may be changed in up-down and left-right directions by fixing one or some of axes of the plurality of joint portions forming the support section 6 and by moving other axes. Specifically, the electric visual field movement mode (XY operation mode) is an operation mode in which the imaging visual field of the capturing unit 21 may be changed in the up-down and left-right directions by fixing the fourth axis $O_1$ to the sixth axis $O_6$ and by electrically moving only the second axis $O_2$ and the third axis $O_3$.

A pivot operation mode included in the electric visual field movement mode is a circling operation according to which the microscope unit 5 moves circularly on a surface of a cone by movement of the support section 6. Here, an apex of the cone is fixed at an arbitrary point in the center direction of the imaging visual field of the capturing unit 21. This operation is also referred to as a point lock operation. A circulating axis in the pivot operation mode is a center axis in a height direction of the cone. In the pivot operation mode, a distance between the fixed point and the capturing unit 21 is maintained constant. At the time of a surgery, a surgical site is selected as the fixed point, for example. In such a pivot operation mode, a surgical site may be observed from different angles but at an equal distance, and thus, a user may accurately grasp the surgical site.

As the electric visual field movement mode, operation modes other than the XY operation mode and the pivot operation mode may be further included.

The first input unit 26 receives input of an operation for moving the capturing area by moving the capturing unit 21. Specifically, the first input unit 26 receives input of operation instructions for the capturing unit 21 and the drive unit 24, and moves the capturing unit 21. The first input unit 26 includes the arm operation switch 26a for receiving input for releasing the electromagnetic brake of the drive unit 24 and for specifying the all free mode, a focus switch and a zoom switch for receiving input for a focus operation and a zoom operation of the capturing unit 21, respectively, an electric visual field movement mode switch for receiving input for specifying the electric visual field movement mode, and a power-assist switch for receiving input for specifying a power-assist mode. As illustrated in FIG. 2, various switches, buttons, and the like configuring the first input unit 26 are provided on the side surface of the microscope unit 5. Incidentally, FIG. 2 illustrates only a part of the various switches, buttons, and the like configuring the first input unit 26. Furthermore, a description is given with reference to FIG. 2, assuming that the first input unit 26 is provided on the side surface of the microscope unit 5, but such a case is not restrictive. For example, a foot switch separate from the microscope unit 5 may be provided as the first input unit 26, and input specifying the all free mode or the focus and zoom operations of the capturing unit 21 may be received according to operation by a foot of a surgeon.

The imaging visual field, or the capturing area, is changed according to an operation on the first input unit 26, and a change in the capturing area includes movement of the imaging visual field in the all free mode and the electric visual field movement mode, a change in a size of the imaging visual field due to a zoom operation, and the like.

The first control unit 27 controls operation of the capturing unit 21 and the drive unit 24 according to an operation instruction input to the first input unit 26 or an operation instruction input from the control device 9 described later. Furthermore, the first control unit 27 integrally controls the observation device 2 in coordination with a second control unit 94 of the control device 9 described later. The first control unit 27 is configured by using a CPU, an ASIC, or the like.

Configuration of Control Device

Next, a functional configuration of the control device 9 will be described.

The control device 9 includes an image processing unit 91, an input unit 92, a recording unit 93, and a second control unit 94.

The image processing unit 91 generates a display image (video signal), for display, to be displayed by the display device 8, by performing O/E conversion on an imaging signal, which is an optical signal transmitted from the observation device 2, and by performing predetermined image processing, which may include various types of image processing, such as color correction, color enhancement, contour enhancement, and mask processing, for example. The image processing unit 91 is configured by using a CPU, an ASIC, an FPGA, or the like.

The input unit 92 is implemented by using an operator interface such as a keyboard, a mouse, or a touch panel, and receives input of various pieces of information.

The recording unit 93 is configured by using a semiconductor memory such as a flash memory or a dynamic random access memory (DRAM), and temporarily records various programs to be executed by the medical observation system 1 and data that is being processed.

The second control unit 94 integrally controls each unit of the medical observation system 1. The second control unit 94 is implemented by using a general-purpose processor, such as a CPU, or a dedicated processor, such as various calculation circuits for achieving specific functions, such as an ASIC, the processors including an internal memory (not illustrated) recording programs. An FPGA, which is a type of programmable integrated circuit, may be used to configure the second control unit 94. Incidentally, when the FPGA is, a memory storing configuration data may be provided, and the FPGA, which is a programmable integrated circuit, may be configured by the configuration data read from the memory. The second control unit 94 includes a drive controller 941, an illumination controller 942, a light projection controller 943, and a display controller 944.

The drive controller 941 controls driving of the support section 6. Specifically, the drive controller 941 controls driving of each actuator and the electromagnetic brake of the support section 6 according to operation contents received by the first input unit 26 or the input unit 92.

The illumination controller 942 controls illumination light that is emitted by the light emitting unit 22.

The light projection controller 943 controls light that is projected by the light projection unit 23.

The display controller 944 controls a display mode of the display device 8 by controlling the image processing unit 91. Specifically, the display controller 944 notifies information indicating that the observation device 2 is performing adjustment of light emission by causing the display device 8 to superimpose the information on an image being displayed.

Correspondence Relationship Between Position of Microscope Unit and Capturing Area Next, a correspondence relationship between the microscope unit 5 (the capturing unit 21) and the capturing area will be described.

Figure 4:
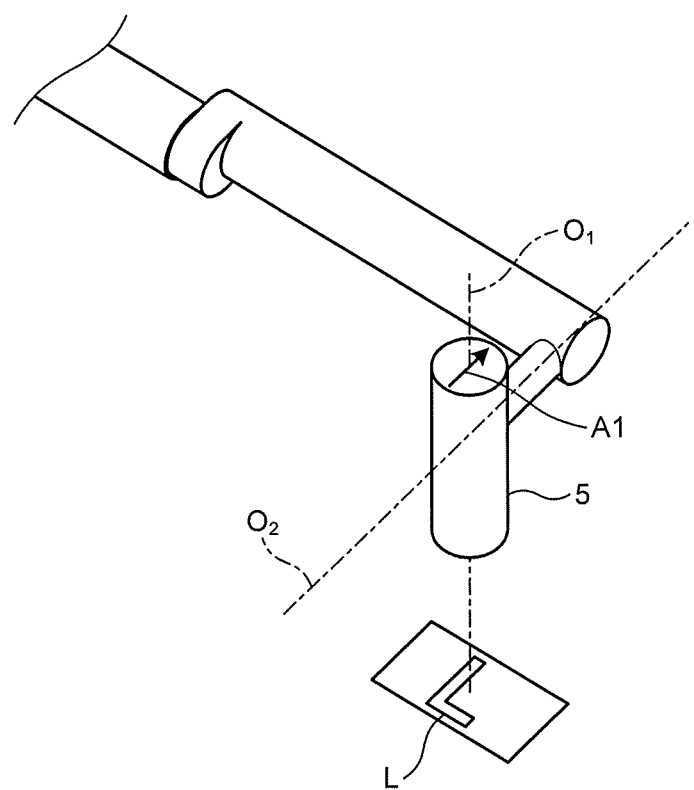
FIG. 4 is a diagram illustrating a positional relationship between the microscope unit and an observation target.

FIG. 4 is a diagram illustrating a positional relationship between the microscope unit and the observation target. According to the positional relationship in FIG. 4, an up direction A1 of the microscope unit 5 coincides with an up direction of a letter L drawn on the observation target.

Figure 5:
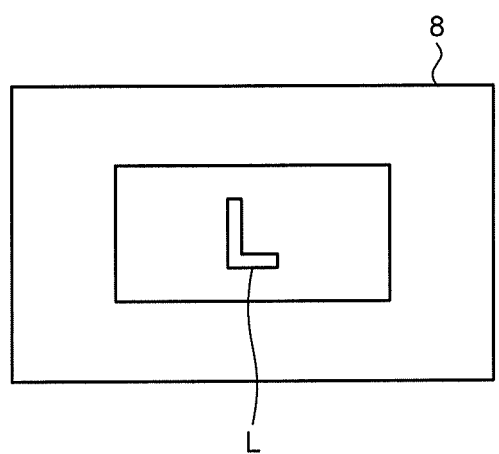
FIG. 5 is a diagram illustrating an image that is displayed on a display device in the positional relationship in FIG. 4.

FIG. 5 is a diagram illustrating an image that is displayed on the display device in the case of the positional relationship in FIG. 4. As illustrated in FIG. 5, when the up direction A1 of the microscope unit 5 and the up direction of the letter L drawn on the observation target coincide with each other, an up direction of the screen of the display device 8 and the up direction of the letter L displayed on the display device 8 coincide with each other.

Figure 6:
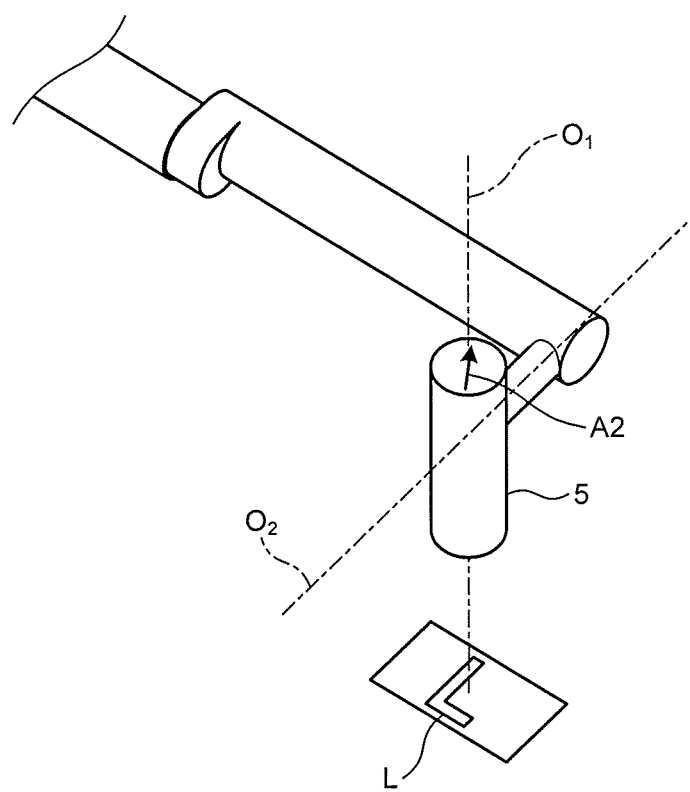
FIG. 6 is a diagram illustrating a positional relationship between the microscope unit and the observation target.

FIG. 6 is a diagram illustrating a positional relationship between the microscope unit and the observation target. According to the positional relationship in FIG. 6, an up direction A2 of the microscope unit 5 is tilted with respect to the up direction of the letter L drawn on the observation target.

Figure 7:
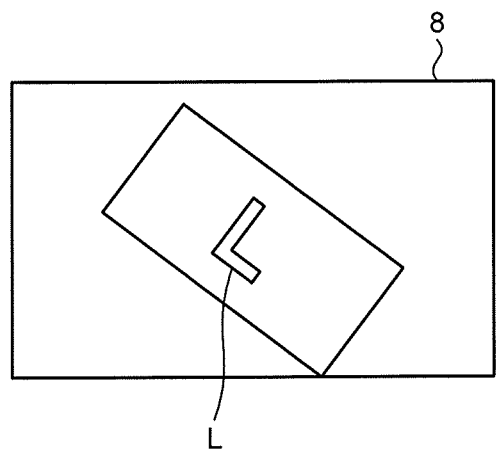
FIG. 7 is a diagram illustrating an image that is displayed on the display device in the positional relationship in FIG. 6.

FIG. 7 is a diagram illustrating an image that is displayed on the display device in the case of the positional relationship in FIG. 6. As illustrated in FIG. 7, when the up direction A2 of the microscope unit 5 is tilted with respect to the up direction of the letter L drawn on the observation target, the up direction of the letter L that is displayed on the display device 8 is tilted according to the aforementioned tilt with respect to the up direction of the screen of the display device 8.

As described with reference to FIGS. 4 to 7, the up direction of the image that is displayed on the display device 8 is determined based on the up direction of the microscope unit 5, but it is difficult for a surgeon and the like to intuitively grasp such a relationship. Furthermore, in the past, a surgeon or the like has had to recognize, using senses, the size of the capturing area that is captured by the microscope unit 5.

Function of Light Projection Unit

Figure 8:
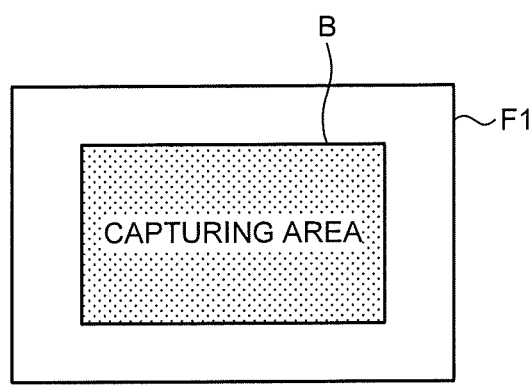
FIG. 8 is a diagram illustrating a pattern that is shown on the observation target due to projection of light by a light projection unit according to the first embodiment.

FIG. 8 is a diagram illustrating a pattern that is shown on the observation target due to projection of light by the light projection unit according to the first embodiment. As illustrated in FIG. 8, the light projection unit 23 projects, on the observation target, a frame F1 for enabling recognition of the capturing area B, in relation to the capturing state of the capturing unit 21 of the microscope unit 5. The frame F1 is a rectangular frame that is arranged outside the capturing area B, in a periphery of the capturing area B, and that surrounds the capturing area B. This enables a surgeon and the like to intuitively recognize the capturing area. Because the frame F1 is arranged outside the capturing area B and does not affect the image that is displayed on the display device 8, it is prevented that the light projection unit 23 interferes with observation by the medical observation system 1.

The first embodiment achieves the medical observation system 1 that allows an operator to intuitively recognize the capturing area B by looking at a pattern that is shown on the observation target due to projection of light by the light projection unit 23.

The light projection unit 23 may constantly project light, but may alternatively project light according to an instruction from an operator, such as input on the first input unit 26 or the input unit 92. Namely, it is sufficient that the light projection unit 23 projects light on the observation target when a surgeon and the like want to check the capturing area B. With this, power consumption may be reduced in this case, compared to where light is constantly projected. Furthermore, the light projection unit 23 may project light while the first input unit 26 is receiving input. Because the light projection unit 23 projects light when the first input unit 26 receives input, so that the capturing area B is changed, a surgeon and the like may intuitively recognize that the capturing area B is to be changed, and power consumption may be reduced.

When a zoom operation is performed in the capturing unit 21 by operation to the first input unit 26, the capturing area B in FIG. 8 is enlarged or reduced. The light projection unit 23 may change a shape or a position of light to be projected on the observation target, according to a size of the capturing area B. Specifically, the light projection unit 23 may change the shape of the light to be projected on the observation target in such a way that a distance from the outer circumference of the capturing area B to the frame F1 becomes constant. Alternatively, the light projection unit 23 may make the distance from the outer circumference of the capturing area B to the frame F1 smaller, the smaller the size of the capturing area B becomes (i.e., the higher a zoom magnification of the capturing unit 21 becomes).

When the capturing area B is enlarged and the light is positioned within the capturing area B, the light projection unit 23 may perform projection in such a way that the light is positioned outside the capturing area B. In other words, the light projection unit 23 may temporarily project light within the capturing area B. This is because it is sufficient that the light projection unit 23 projects light outside the capturing area B when a surgeon and the like perform a surgery.

First Modification

Figure 9:
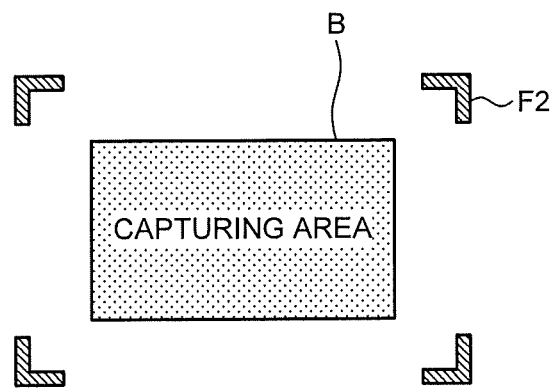
FIG. 9 is a diagram illustrating a pattern that is shown on the observation target due to projection of light by the light projection unit according to a first modification of the first embodiment.

FIG. 9 is a diagram illustrating a pattern that is shown on the observation target due to projection of light by the light projection unit according to a first modification of the first embodiment. As illustrated in FIG. 9, the light projection unit 23 according to the first modification of the first embodiment projects frames F2 on the observation target. The frames F2 are L-shaped frames that are arranged outside the capturing area B, in peripheries of four corners of the capturing area B.

Second Modification

Figure 10:
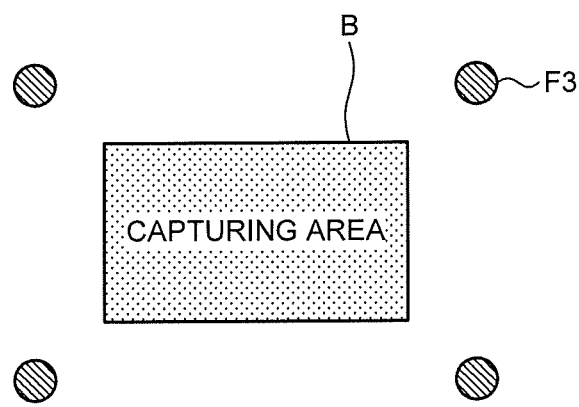
FIG. 10 is a diagram illustrating a pattern that is shown on the observation target due to projection of light by the light projection unit according to a second modification of the first embodiment.

FIG. 10 is a diagram illustrating a pattern that is shown on the observation target due to projection of light by the light projection unit according to a second modification of the first embodiment. As illustrated in FIG. 10, the light projection unit 23 according to the second modification of the first embodiment projects frames F3 on the observation target. The frames F3 are dots that are arranged outside the capturing area B, in peripheries of four corners of the capturing area B.

Third Modification

Figure 11:
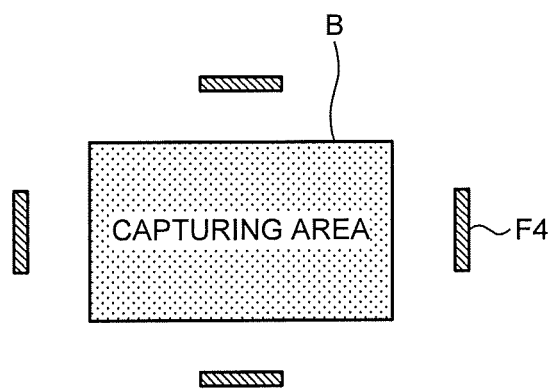
FIG. 11 is a diagram illustrating a pattern that is shown on the observation target due to projection of light by the light projection unit according to a third modification of the first embodiment.

FIG. 11 is a diagram illustrating a pattern that is shown on the observation target due to projection of light by the light projection unit according to a third modification of the first embodiment. As illustrated in FIG. 11, the light projection unit 23 according to the third modification of the first embodiment projects frames F4 on the observation target. The frames F4 are line segments that are arranged outside the capturing area B, the line segments being arranged in peripheries of respective sides of the capturing area B while being parallel to the respective sides.

The first to third modifications achieve the medical observation system 1 that allows an operator to intuitively recognize the capturing area B by looking at the pattern that is shown on the observation target due to projection of light by the light projection unit 23. As described in the first to third modifications, the shape of the light that is projected by the light projection unit 23 is not particularly limited as long as the capturing area B can be recognized.

Fourth Modification

Figure 12:
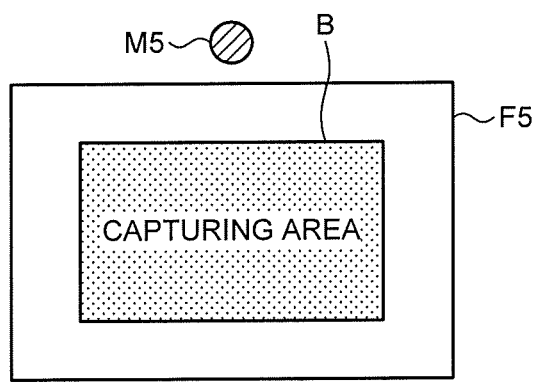
FIG. 12 is a diagram illustrating a pattern that is shown on the observation target due to projection of light by the light projection unit according to a fourth modification of the first embodiment.

FIG. 12 is a diagram illustrating a pattern that is shown on the observation target due to projection of light by the light projection unit according to a fourth modification of the first embodiment. As illustrated in FIG. 12, the light projection unit 23 according to the fourth modification of the first embodiment projects a frame F5. The frame F5 is a rectangular frame that is arranged outside the capturing area B, in a periphery of the capturing area B, and that surrounds the capturing area B. The light projection unit 23 also projects a marker M5 that enables recognition of top/bottom of the capturing area B, in relation to the capturing state of the capturing unit 21 of the microscope unit 5. The marker M5 is a dot that is projected in a periphery of a center of an upper long side of the frame F5. This enables a surgeon and the like to intuitively grasp a correspondence relationship between the up direction of the microscope unit 5 and an up direction of the capturing area B.

Incidentally, the light projection unit 23 may change the position of the light that is projected on the observation target, according to the size of the capturing area B that is changed according to a zoom operation. Specifically, the light projection unit 23 may change the position where the marker M5 is projected, in such a way that a distance from the outer circumference of the capturing area B to the marker M5 becomes constant.

Fifth Modification

Figure 13:
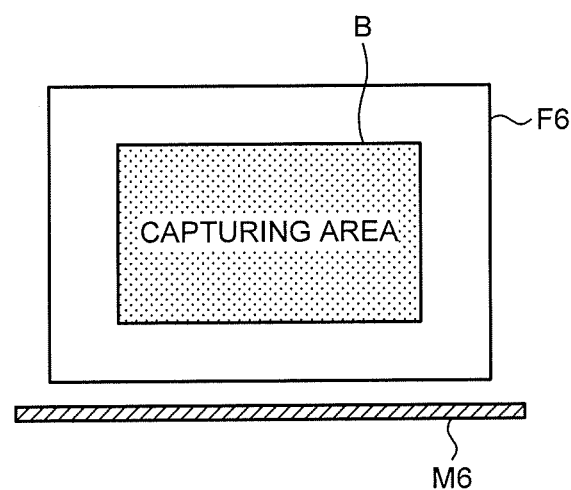
FIG. 13 is a diagram illustrating a pattern that is shown on the observation target due to projection of light by the light projection unit according to a fifth modification of the first embodiment.

FIG. 13 is a diagram illustrating a pattern that is shown on the observation target due to projection of light by the light projection unit according to a fifth modification of the first embodiment. As illustrated in FIG. 13, the light projection unit 23 according to the fifth modification of the first embodiment projects a frame F6. The frame F6 is a rectangular frame that is arranged outside the capturing area B, in a periphery of the capturing area B, and that surrounds the capturing area B. The light projection unit 23 also projects a marker M6 that enables recognition of top/bottom of the capturing area B, in relation to the capturing state of the capturing unit 21 of the microscope unit 5. The marker M6 is a line segment that is projected along a lower long side of the frame F6.

The fourth and fifth modifications achieve the medical observation system 1 that allows an operator to intuitively recognize the up direction and the size of the capturing area B by looking at the pattern that is shown on the observation target due to projection of light by the light projection unit 23. As described in the fourth and fifth modifications, the shape of the marker is not particularly limited as long as the top/bottom of the capturing area B may be intuitively recognized.

Sixth Modification

Figure 14:
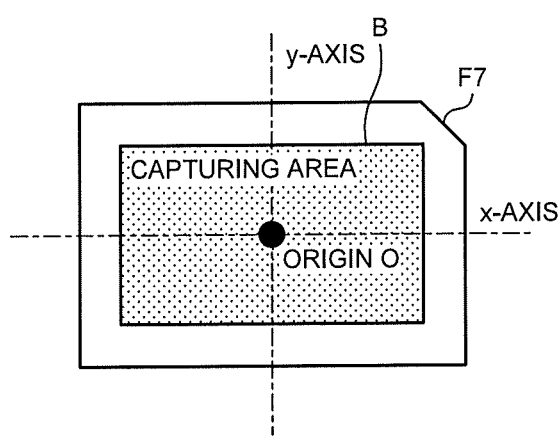
FIG. 14 is a diagram illustrating a pattern that is shown on the observation target due to projection of light by the light projection unit according to a sixth modification of the first embodiment.

FIG. 14 is a diagram illustrating a pattern that is shown on the observation target due to projection of light by the light projection unit according to a sixth modification of the first embodiment. As illustrated in FIG. 14, the light projection unit 23 according to the sixth modification of the first embodiment projects a frame F7. The frame F7 is a pentagon obtained by linearly cutting off one vertex of a rectangle that surrounds the outer circumference of the capturing area B, and a side with the cut-off vertex, of two long sides, corresponds to the up direction of the microscope unit 5.

Seventh Modification

Figure 15:
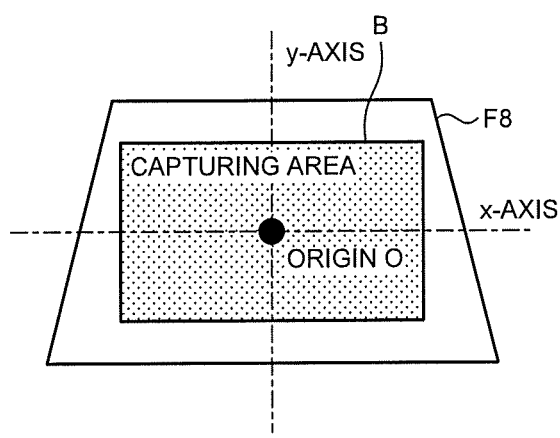
FIG. 15 is a diagram illustrating a pattern that is shown on the observation target due to projection of light by the light projection unit according to a seventh modification of the first embodiment.

FIG. 15 is a diagram illustrating a pattern that is shown on the observation target due to projection of light by the light projection unit according to a seventh modification of the first embodiment. As illustrated in FIG. 15, the light projection unit 23 according to the seventh modification of the first embodiment projects a frame F8. The frame F8 is an isosceles trapezoidal frame that surrounds the outer circumference of the capturing area B and that is narrower on an upper side, and an up direction thereof corresponds to the up direction of the microscope unit 5.

The sixth and seventh modifications achieve the medical observation system 1 that allows an operator to intuitively recognize the up direction and the size of the capturing area B by looking at the pattern that is shown on the observation target due to projection of light by the light projection unit 23. As described in the sixth and seventh modifications, it is possible to intuitively recognize the up direction of the microscope unit 5 by changing the shape of the frame so that a part on the up direction side and the opposite part on a downward direction side are different from each other.

Eighth Modification

Figure 16:
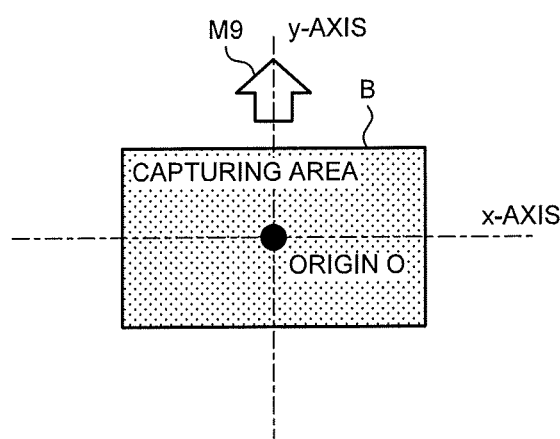
FIG. 16 is a diagram illustrating a pattern that is shown on the observation target due to projection of light by the light projection unit according to an eighth modification of the first embodiment.

FIG. 16 is a diagram illustrating a pattern that is shown on the observation target due to projection of light by the light projection unit according to an eighth modification of the first embodiment. As illustrated in FIG. 16, the light projection unit 23 according to the eighth modification of the first embodiment projects a marker M9. The marker M9 is an arrow that is arranged outside and above the capturing area B, in a periphery of the capturing area B, and that is directed towards the up direction of the microscope unit 5.

Ninth Modification

Figure 17:
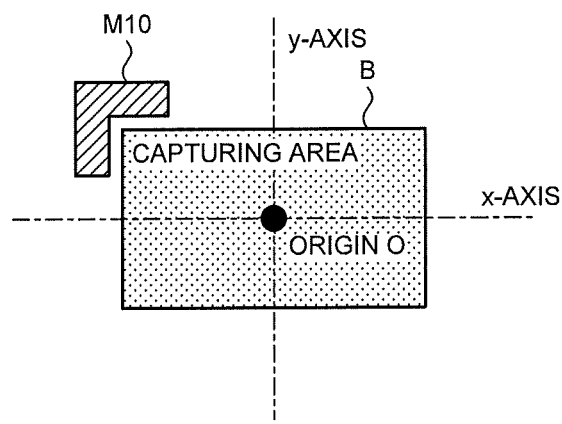
FIG. 17 is a diagram illustrating a pattern that is shown on the observation target due to projection of light by the light projection unit according to a ninth modification of the first embodiment.

FIG. 17 is a diagram illustrating a pattern that is shown on the observation target due to projection of light by the light projection unit according to a ninth modification of the first embodiment. As illustrated in FIG. 17, the light projection unit 23 according to the ninth modification of the first embodiment projects a marker M10. The marker M10 is an L-shaped mark that is arranged outside the capturing area B, in a periphery of one of the four corners of the capturing area B.

The eighth and ninth modifications achieve the medical observation system 1 that allows an operator to intuitively recognize the up direction and an approximate position of the capturing area B by looking at the pattern that is shown on the observation target due to projection of light by the light projection unit 23. As with the eighth and ninth modifications, a single marker may be shown which makes only the up direction of the microscope unit 5 recognizable.

Tenth Modification

Figure 18:
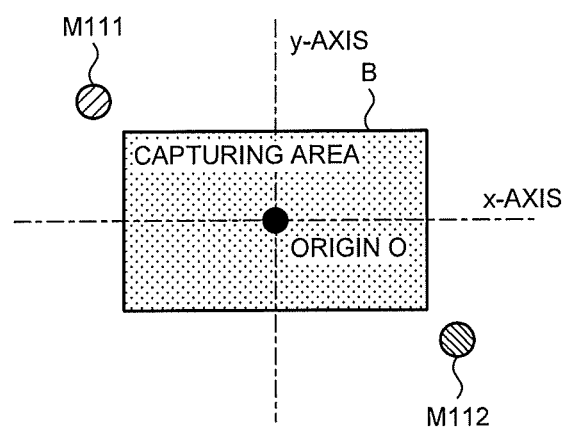
FIG. 18 is a diagram illustrating a pattern that is shown on the observation target due to projection of light by the light projection unit according to a tenth modification of the first embodiment.

FIG. 18 is a diagram illustrating a pattern that is shown on the observation target due to projection of light by the light projection unit according to a tenth modification of the first embodiment. As illustrated in FIG. 18, the light projection unit 23 according to the tenth modification of the first embodiment projects a marker M111 and a marker M112. In the following, a center of the capturing area B is taken as an origin O; a straight line that is parallel to long sides of the capturing area B and that passes through the origin O is taken as an x-axis; and a straight line that is parallel to short sides of the capturing area B and that passes through the origin O is taken as a y-axis. The marker M111 and the marker M112 are dots of different colors, and are positioned outside the capturing area B, in peripheries of two of the four corners of the capturing area B, while being diagonally opposite to each other across the origin O. Incidentally, in FIG. 18 and following drawings, a difference in colors is expressed by a difference in hatching patterns. Furthermore, the markers may be different in size, shape, pattern, flashing pattern or the like, instead of in color.

Eleventh Modification

Figure 19:
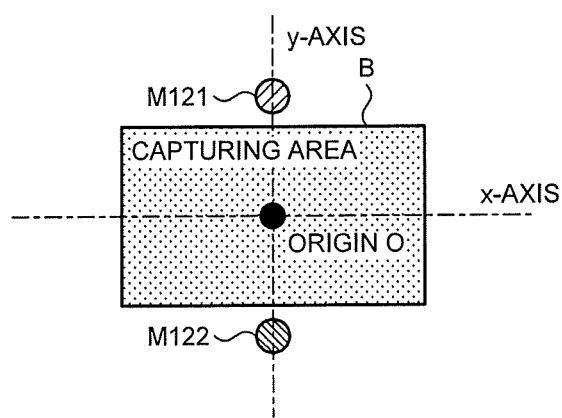
FIG. 19 is a diagram illustrating a pattern that is shown on the observation target due to projection of light by the light projection unit according to an eleventh modification of the first embodiment.

FIG. 19 is a diagram illustrating a pattern that is shown on the observation target due to projection of light by the light projection unit according to an eleventh modification of the first embodiment. As illustrated in FIG. 19, the light projection unit 23 according to the eleventh modification of the first embodiment projects a marker M121 and a M122. The marker M121 and the marker M122 are dots of different colors, and are positioned outside the capturing area B, in peripheries of centers of the long sides of the capturing area B, while being on the y-axis so as to be opposite to each other across the origin O.

Twelfth Modification

Figure 20:
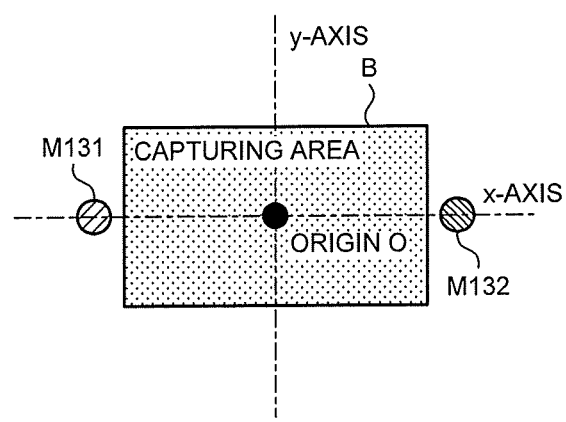
FIG. 20 is a diagram illustrating a pattern that is shown on the observation target due to projection of light by the light projection unit according to a twelfth modification of the first embodiment.

FIG. 20 is a diagram illustrating a pattern that is shown on the observation target due to projection of light by the light projection unit according to a twelfth modification of the first embodiment. As illustrated in FIG. 20, the light projection unit 23 according to the twelfth modification of the first embodiment projects a marker M131 and a marker M132. The marker M131 and the marker M132 are dots of different colors, and are positioned outside the capturing area B, in peripheries of centers of the short sides of the capturing area B, while being on the x-axis so as to be opposite to each other across the origin O.

The tenth to twelfth modifications achieve the medical observation system 1 that allows an operator to intuitively recognize the up direction and the size of the capturing area B by looking at the pattern that is shown on the observation target due to projection of light by the light projection unit 23. As described in the tenth to twelfth modifications, it is possible to recognize the up direction of the microscope unit 5 and the approximate size of the capturing area B by arranging markers of different colors at positions that are point-symmetric across the origin O. According to such configurations, the markers are dots, and do not have to have complex shapes, and thus, the light projection unit 23 may be realized by a simple configuration.

Thirteenth Modification

Figure 21:
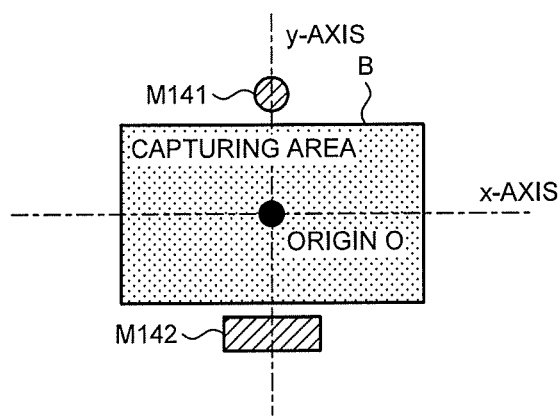
FIG. 21 is a diagram illustrating a pattern that is shown on the observation target due to projection of light by the light projection unit according to a thirteenth modification of the first embodiment.

FIG. 21 is a diagram illustrating a pattern that is shown on the observation target due to projection of light by the light projection unit according to a thirteenth modification of the first embodiment. As illustrated in FIG. 21, the light projection unit 23 according to the thirteenth modification of the first embodiment projects a marker M141 and a marker M142. The marker M141 and the marker M142 are of a same color but of different shapes. Namely, the marker M141 is a dot and the marker M142 is a line segment. The makers M141, M142 are arranged outside the capturing area B, in peripheries of the centers of the long sides, while being on the y-axis so as to be opposite to each other across the origin O.

Fourteenth Modification

Figure 22:
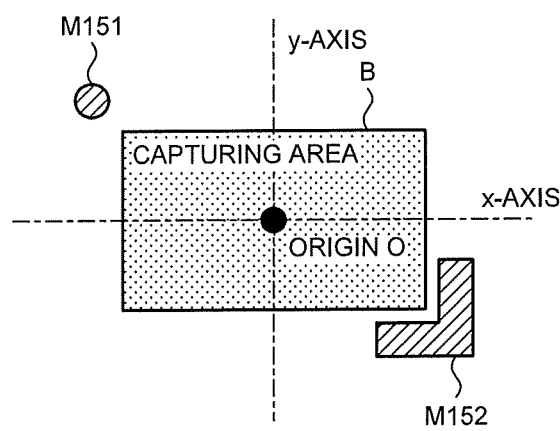
FIG. 22 is a diagram illustrating a pattern that is shown on the observation target due to projection of light by the light projection unit according to a fourteenth modification of the first embodiment.

FIG. 22 is a diagram illustrating a pattern that is shown on the observation target due to projection of light by the light projection unit according to a fourteenth modification of the first embodiment. As illustrated in FIG. 22, the light projection unit 23 according to the fourteenth modification of the first embodiment projects a marker M151 and a marker M152. The marker M151 and the marker M152 are of a same color but with different shapes. Namely, the marker M151 is a dot and the marker M152 is an L-shaped mark. The marker M151, M152 are arranged outside the capturing area B, in peripheries of two of the four corners of the capturing area B, while being diagonally opposite to each other across the origin O.

Fifteenth Modification

Figure 23:
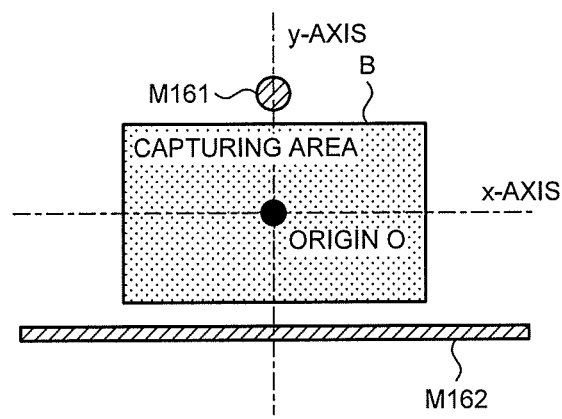
FIG. 23 is a diagram illustrating a pattern that is shown on the observation target due to projection of light by the light projection unit according to a fifteenth modification of the first embodiment.

FIG. 23 is a diagram illustrating a pattern that is shown on the observation target due to projection of light by the light projection unit according to a fifteenth modification of the first embodiment. As illustrated in FIG. 23, the light projection unit 23 according to the fifteenth modification of the first embodiment projects a marker M161 and a marker M162. The marker M161 and the marker M162 are of a same color but with different shapes. Namely, the marker M161 is a dot and the marker M162 is a line segment. The markers M161 and M162 are arranged outside the capturing area B, in peripheries of centers of the long sides, while being on the y-axis so as to be opposite to each other across the origin O. A center of the marker M162 is on the y-axis, and the marker M162 is slightly longer than a width of the capturing area B. This enables an operator to intuitively recognize an approximate width of the capturing area B.

Sixteenth Modification

Figure 24:
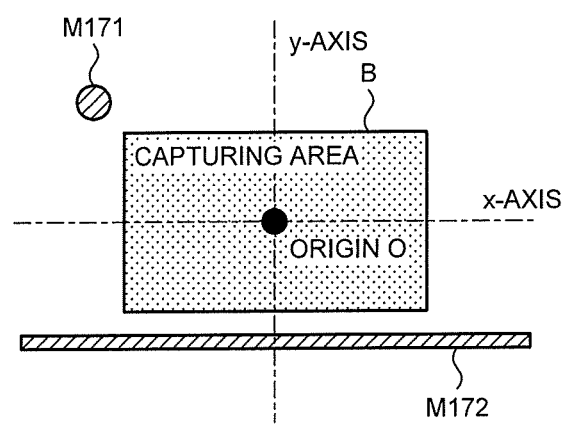
FIG. 24 is a diagram illustrating a pattern that is shown on the observation target due to projection of light by the light projection unit according to a sixteenth modification of the first embodiment.

FIG. 24 is a diagram illustrating a pattern that is shown on the observation target due to projection of light by the light projection unit according to a sixteenth modification of the first embodiment. As illustrated in FIG. 24, the light projection unit 23 according to the sixteenth modification of the first embodiment projects a marker M171 and a marker M172. The marker M171 and the marker M172 are of a same color but with different shapes. Namely, the marker M171 is a dot and the marker M172 is a line segment. The markers M171, M172 are positioned outside the capturing area B while facing each other across the origin O and the x-axis. A center of the marker M172 is on the y-axis, and the marker M172 is slightly longer than the width of the capturing area B. This enables an operator to intuitively recognize an approximate width of the capturing area B.

The thirteenth to sixteenth modifications achieve the medical observation system 1 that allows an operator to intuitively recognize the up direction and the size of the capturing area B by looking at the pattern that is shown on the observation target due to projection of light by the light projection unit 23. As described in the thirteenth to sixteenth modifications, it is possible to recognize the up direction of the microscope unit 5 and the approximate size of the capturing area B by arranging the markers of different shapes.

Seventeenth Modification

Figure 25:
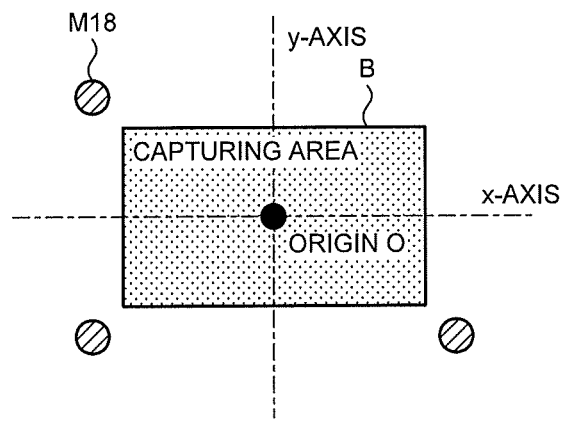
FIG. 25 is a diagram illustrating a pattern that is shown on the observation target due to projection of light by the light projection unit according to a seventeenth modification of the first embodiment.

FIG. 25 is a diagram illustrating a pattern that is shown on the observation target due to projection of light by the light projection unit according to a seventeenth modification of the first embodiment. As illustrated in FIG. 25, the light projection unit 23 according to the seventeenth modification of the first embodiment projects markers M18. The markers M18 are dots of a same color that are arranged outside the capturing area B, in peripheries of three of the four corners of the capturing area B.

The seventeenth modification achieves the medical observation system 1 allows an operator to intuitively recognize the up direction and the size of the capturing area B by looking at the pattern that is shown on the observation target due to projection of light by the light projection unit 23. As described in the seventeenth modification, it is possible to recognize the up direction of the microscope unit 5 and the approximate size of the capturing area B by using three markers of a same color.

Eighteenth Modification

Figure 26:
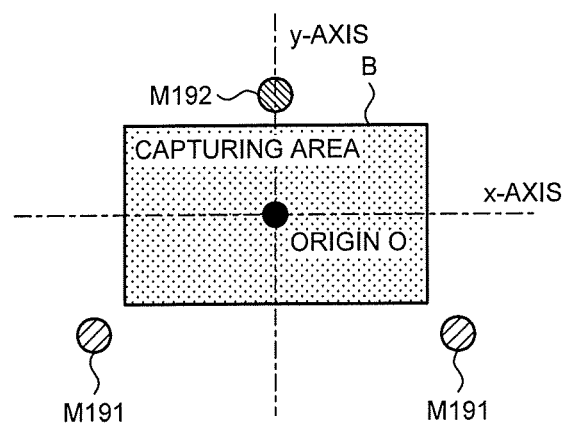
FIG. 26 is a diagram illustrating a pattern that is shown on the observation target due to projection of light by the light projection unit according to an eighteenth modification of the first embodiment.

FIG. 26 is a diagram illustrating a pattern that is shown on the observation target due to projection of light by the light projection unit according to an eighteenth modification of the first embodiment. As illustrated in FIG. 26, the light projection unit 23 according to the eighteenth modification of the first embodiment projects markers M191 and a marker M192. The markers M191 are dots that are arranged outside the capturing area B, in peripheries of two lower corners of the four corners of the capturing area B. The marker M192 is a dot of a different color from the markers M191, and is arranged outside the capturing area B, in a periphery of a center of the upper long side.

The eighteenth modification achieves the medical observation system 1 allows an operator to intuitively recognize the up direction and the size of the capturing area B by looking at the pattern that is shown on the observation target due to projection of light by the light projection unit 23. As described in the eighteenth modification, it is possible to recognize the up direction of the microscope unit 5 and the approximate size of the capturing area B by using two markers of a same color and a single marker of a different color.

According to the seventeenth and eighteenth modifications, the markers are dots, and do not have to have complex shapes, and thus, the light projection unit 23 may be realized by a simple configuration.

Nineteenth Modification

Figure 27:
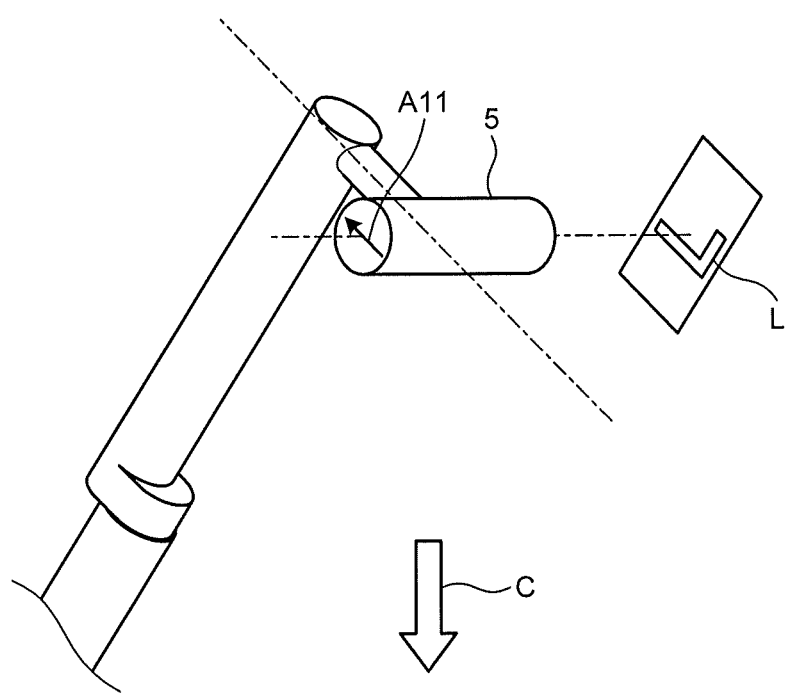
FIG. 27 is a diagram illustrating a positional relationship between the microscope unit and the observation target.

FIG. 27 is a diagram illustrating a positional relationship between the microscope unit and the observation target. A direction C illustrated in FIG. 27 is the vertically downward direction, and a direction A11 is the up direction of the capturing unit 21 of the microscope unit 5. In the nineteenth modification, the first detection unit 25 (FIG. 3) detects an angle formed by the up direction of the capturing unit 21 and the vertically downward direction C.

Figure 28:
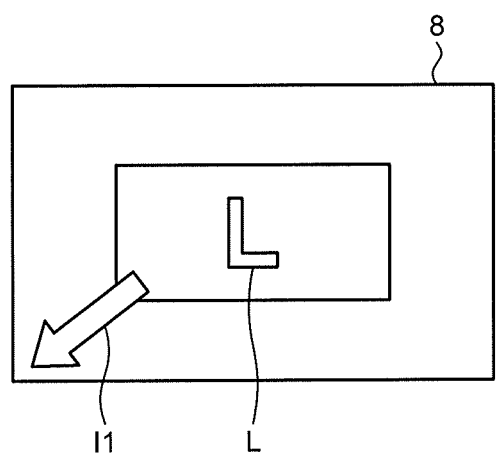
FIG. 28 is a diagram illustrating an image that is displayed on the display device in the positional relationship in FIG. 27.

FIG. 28 is a diagram illustrating an image that is displayed on the display device in the positional relationship in FIG. 27. As illustrated in FIG. 28, the image processing unit 91 generates an image, which is an image captured by the capturing unit 21, on which an indicator I1 indicating the vertically downward direction C is superimposed. This enables a surgeon and the like to recognize the direction of the capturing unit 21 by looking at the screen of the display device 8. In this manner, information allowing recognition of the capturing state of the capturing unit 21 of the microscope unit 5 may be displayed on the display device 8 side.

Additionally, the image processing unit 91 may generate the image which is the image captured by the capturing unit 21 on which the indicator I1 indicating the vertically downward direction C is superimposed, in a case where the angle formed by the vertically downward direction C and the direction A11 exceeds a threshold.

The image processing unit 91 may constantly generate the image on which the indicator I1 is superimposed, or may generate the image, which is the image captured by the capturing unit 21, on which the indicator I1 indicating the vertically downward direction C is superimposed, according to an instruction from an operator. Specifically, the image processing unit 91 may generate the image on which the indicator I1 is superimposed, according to an instruction from an operator, such as an input on the first input unit 26 or the input unit 92. Alternatively, the image processing unit 91 may generate the image, which is the image captured by the capturing unit 21, on which the indicator I1 indicating the vertically downward direction C is superimposed, while the arm operation switch 26*a* of the first input unit 26 is receiving input.

Twentieth Modification

Figure 29:
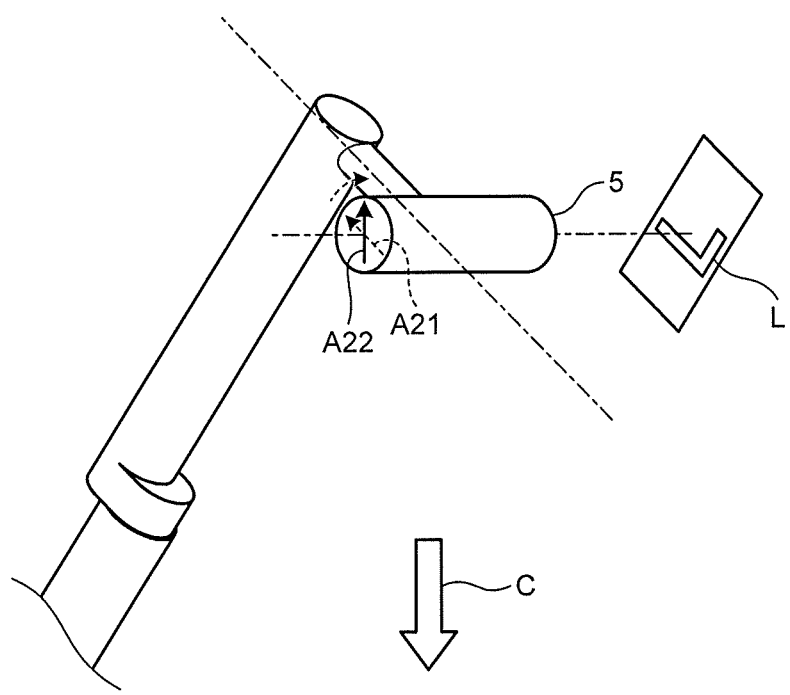
FIG. 29 is a diagram illustrating a positional relationship between the microscope unit and the observation target.

FIG. 29 is a diagram illustrating a positional relationship between the microscope unit and the observation target. Referring to FIG. 29, the microscope unit 5 (capturing unit 21) is driven under control of the drive controller 941 (FIG. 3) so that the up direction of the capturing unit 21 is opposite to the vertically downward direction C. Specifically, when the capturing unit 21 of the microscope unit 5 is directed towards a direction A21 different from an opposite direction of the vertically downward direction C, the drive controller 941 causes the up direction of the capturing unit 21 to coincide with a direction A22 which is the opposite direction of the vertically downward direction C. In other words, the drive controller 941 controls driving of each actuator of the support section 6, and rotates the microscope unit 5 in such a way that the up direction of the capturing unit 21 becomes the direction A22.

Figure 30:
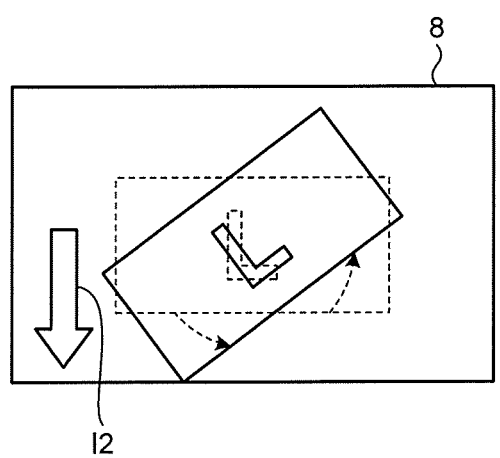
FIG. 30 is a diagram illustrating an image that is displayed on the display device in the positional relationship in FIG. 29.

FIG. 30 is a diagram illustrating an image displayed on the display device in the case of the positional relationship in FIG. 29. As illustrated in FIG. 30, when the drive controller 941 rotates the up direction of the capturing unit 21 from the direction A21 to the direction A22, a downward direction of the display device 8 and a direction of an indicator 12 corresponding to the vertically downward direction C are caused to coincide with each other. This enables an operator to easily change a capturing direction of the capturing unit 21 to a horizontal direction.

Incidentally, the drive controller 941 may cause the up direction of the capturing unit 21 to be the opposite direction of the vertically downward direction C, when an angle formed by the vertically downward direction C and the direction A21 exceeds a threshold.

Additionally, the drive controller 941 may cause the up direction of the capturing unit 21 to be the opposite direction of the vertically downward direction C, according to an instruction from an operator. Specifically, the drive controller 941 may cause the up direction of the capturing unit 21 to be the opposite direction of the vertically downward direction C, according to an instruction from an operator, such as an input on the first input unit 26 or the input unit 92.

Second Embodiment

Figure 31:
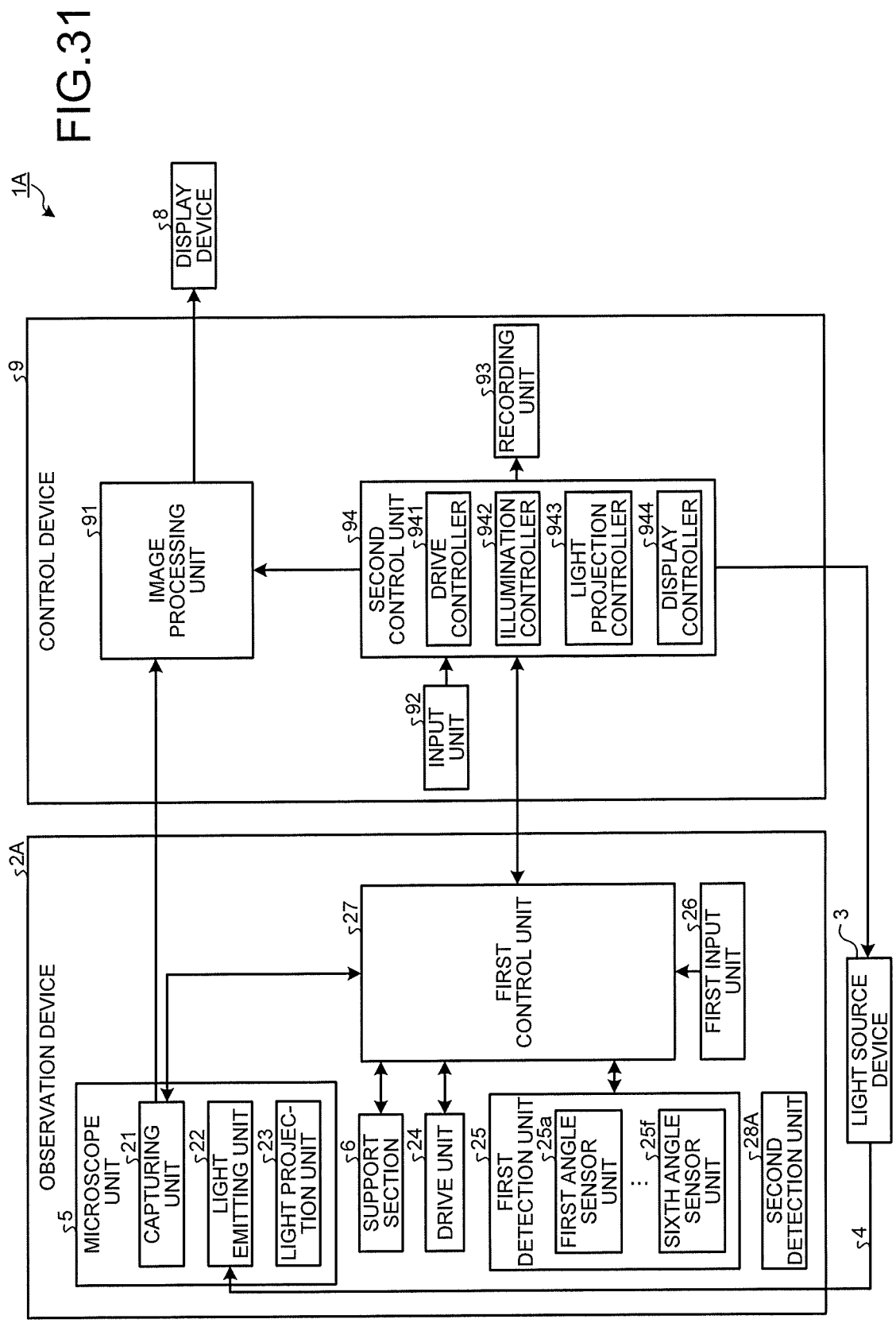
FIG. 31 is a block diagram illustrating a functional configuration of a medical observation system according to a second embodiment.

FIG. 31 is a block diagram illustrating a functional configuration of a medical observation system according to a second embodiment. As illustrated in FIG. 31, a medical observation system 1A includes an observation device 2A, a control device 9, and a display device 8. The observation device 2A includes a microscope unit 5 having a capturing unit 21, and a second detection unit 28A for detecting a position of at least one of a surgeon or an assistant.

Figure 32:
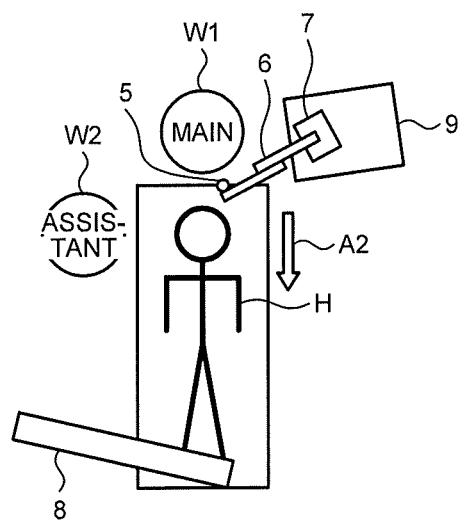
FIG. 32 is a diagram illustrating a positional relationship among an observation target, a capturing unit, a control device, a display device, a surgeon, and an assistant.

FIG. 32 is a diagram illustrating a positional relationship among an observation target, the capturing unit, the control device, the display device, a surgeon, and an assistant. It is assumed that an observation target H, a microscope unit 5 including the capturing unit 21, the control device 9, the display device 8, a surgeon (main operator) W1, and an assistant W2 are in a positional relationship as illustrated in FIG. 32. An up direction of the capturing unit 21 is a direction A2 in FIG. 32.

Figure 33:
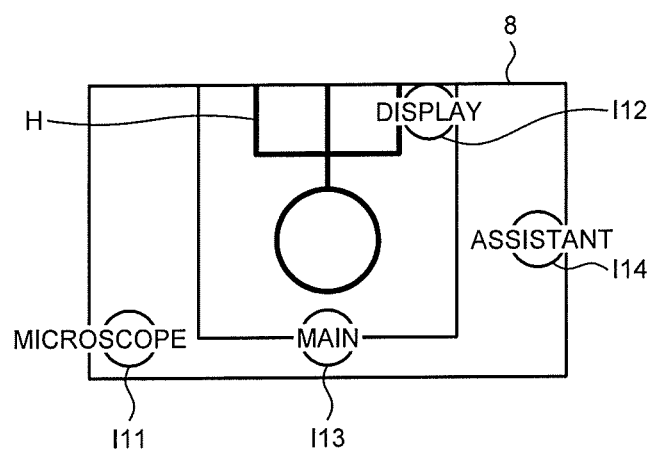
FIG. 33 is a diagram illustrating an image that is displayed on the display device in the positional relationship in FIG. 32.

FIG. 33 is a diagram illustrating an image that is displayed on the display device in the case of the positional relationship in FIG. 32. As illustrated in FIG. 33, the control device 9 generates an image, which is an image captured by the capturing unit 21, on which indicators I11 to I14 indicating positions detected by the second detection unit 28A are superimposed. The indicator I11 indicates the position of the control device 9, the indicator I12 the position of the display device 8, the indicator I13 the position of the surgeon, and the indicator I14 the position of the assistant. Because these indicators I11 to I14 are displayed on the display device 8, the surgeon and the like may recognize the direction of the capturing unit 21 by looking at a screen of the display device 8. In this manner, information enabling recognition of a capturing state of the capturing unit 21 of the microscope unit 5 may be displayed on the display device 8 side.

Incidentally, the control device 9 may also generate an image, which is an image captured by the capturing unit 21, on which an indicator in a form of an arrow or the like is superimposed, the indicator indicating a direction of detection by the second detection unit 28A.

Furthermore, the control device 9 may generate an image, which is an image captured by the capturing unit 21, on which the indicators I11 to I14 indicating detected positions or directions are superimposed, when an angle formed by the vertically downward direction C and the up direction of the capturing unit 21 exceeds a threshold.

Moreover, the control device 9 may generate an image, which is an image captured by the capturing unit 21, on which the indicators I11 to I14 indicating positions or directions detected by the second detection unit 28A are superimposed, according to an instruction from an operator. Specifically, the control device 9 may generate an image, which is an image captured by the capturing unit 21, on which the indicators I11 to I14 indicating positions or directions detected by the second detection unit 28A are superimposed, according to an instruction from an operator, such as an input on the first input unit 26 or the input unit 92.

The control device 9 may generate an image, which is an image captured by the capturing unit 21, on which the indicators I11 to I14 indicating positions or directions detected by the second detection unit 28A are superimposed, while the arm operation switch 26a of the first input unit 26 is receiving input.

Third Embodiment

Figure 34:
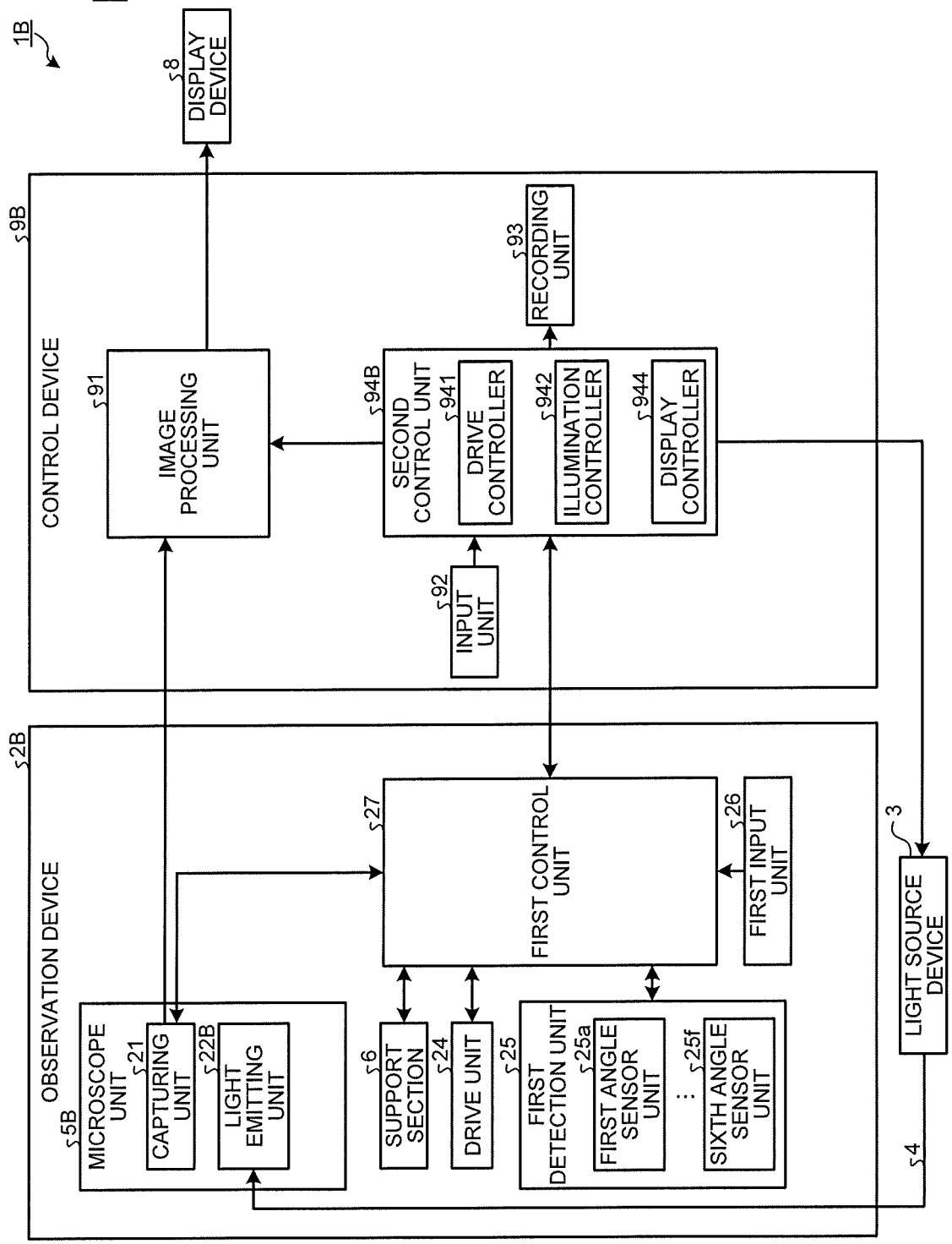
FIG. 34 is a block diagram illustrating a functional configuration of a medical observation system according to a third embodiment.

FIG. 34 is a block diagram illustrating a functional configuration of a medical observation system according to a third embodiment. As illustrated in FIG. 34, in a medical observation system 1B, a microscope unit 5B of an observation device 2B includes a light emitting unit 22B for emitting first illumination light in a capturing direction of a capturing unit 21, but unlike in the first embodiment, a light projection unit is not provided. Furthermore, in the medical observation system 1B, a second control unit 94B of a control device 9B does not include a light projection controller.

The light emitting unit 22B radiates second illumination light on an observation target, outside a capturing area B to be captured by the capturing unit 21 and in a periphery of the capturing area B, the second illumination light being for enabling recognition of a capturing state of the capturing unit 21. Specifically, the light emitting unit 22B emits, to the observation target, second illumination light that enables recognition of top/bottom of the capturing area B.

Figure 35:
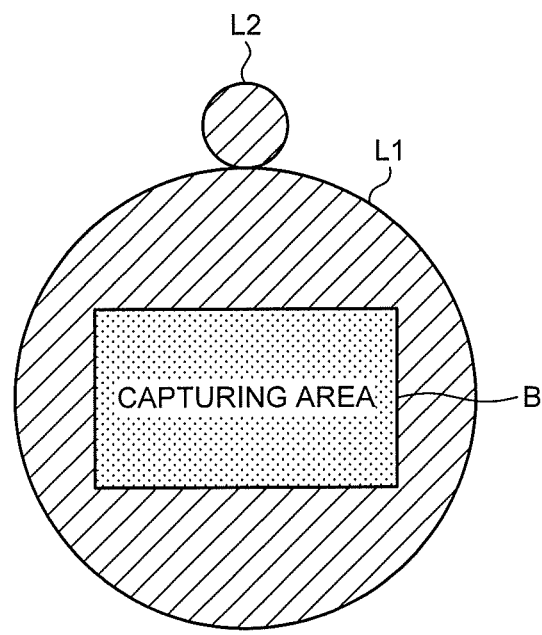
FIG. 35 is a diagram illustrating a pattern that is shown on an observation target due to emission of light by a light emitting unit according to the third embodiment.

FIG. 35 is a diagram illustrating a pattern that is shown on an observation target due to emission of light by the light emitting unit according to the third embodiment. As illustrated in FIG. 35, the light emitting unit 22B radiates the first illumination light L1 on the capturing area B on the observation target, and emits spot-shaped second illumination light L2 outside the first illumination light L1. The second illumination light L2 corresponds to an up direction of the capturing unit 21, and a surgeon and the like are enabled to intuitively recognize the up direction of the capturing area B. Incidentally, in other drawings such as FIG. 8, illumination light (the first illumination light) is radiated by the light emitting unit on the observation target, but the illumination light is omitted from the drawings other than FIG. 35.

In this manner, the second illumination light different from the first illumination light may be generated so as to enable recognition of the up direction of the capturing area B, by arranging a lens or the like at an emitting part of the light emitting unit 22B. According to such a configuration, a light projection unit does not have to be provided, and the configuration in the first embodiment may be further simplified.

According to the present disclosure, a medical observation system may be realized, which enables an operator to intuitively recognize a capturing area.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical observation system comprising:
   an image capture device operable to capture an image of an observation target; and
   a light projector operable to project periphery light on the observation target, outside a capturing area that is captured by the image capture device and in a periphery of the capturing area, the periphery light enabling determination of a capturing state of the image capture device,
   wherein the capturing state of the image capture device includes a direction of the capturing area, which includes a correspondence relationship between an up direction of the captured image that is displayed on a display device and an up direction of the image capture device, wherein the up direction of the image capture device is perpendicular to a first axis of a first joint portion of a support section, and wherein the correspondence relationship includes an angle between the up direction of the image capture device and a reference direction.

2. The medical observation system according to claim 1, wherein the light projection unit projects a pattern that enables recognition of the capturing area.

3. The medical observation system according to claim 2, wherein the light projection unit projects, as the pattern, a frame that enables recognition of a size of the capturing area or a marker that enables recognition of a top or bottom portion of the capturing area.

4. The medical observation system according to claim 1, further comprising
   an interface operable to receive an operation performed by an operator,
   wherein the light projector projects the periphery light according to an instruction that is received from the operator by the interface.

5. The medical observation system according to claim 1, further comprising
   an interface operable to receive an operation for moving the capturing area by moving the image capture device,
   wherein the light projection projects the periphery light while the interface is receiving the input.

6. The medical observation system according to claim 1, further comprising
   an interface operable to receive operations for enlarging and reducing the capturing area,
   wherein the light projector changes a shape or a position of the periphery light according to the size of the capturing area.

7. The medical observation system according to claim 1, further comprising
   an interface operable to receive operations for enlarging and reducing the capturing area,
   wherein the light projector projects the periphery light in such a way that the periphery light is positioned outside the capturing area, when the capturing area is enlarged and the periphery light is positioned within the capturing area.

8. The medical observation system according to claim 1, further comprising:
    circuitry configured to
        detect an angle that is formed by the up direction of the image capture device and a vertically downward direction, the up direction of the image capture device corresponding to an up direction of an image that is captured by the image capture device; and
        generate an image in which an indicator indicating the vertically downward direction is superimposed on the image captured by the image capture device, according to the angle.

9. The medical observation system according to claim 8, wherein, when the angle that is formed by the up direction of the image capture device and the vertically downward direction exceeds a threshold, the circuitry generates an image in which the indicator indicating the vertically downward direction is superimposed on the image captured by the image capture device.

10. The medical observation system according to claim 8, further comprising
    an interface operable to receive an operation performed by an operator,
    wherein the circuitry is configured to generate an image in which the indicator indicating the vertically downward direction is superimposed on the image captured by the image capture device, according to an instruction that is received from the operator by the interface.

11. The medical observation system according to claim 8, further comprising
    an interface operable to receive an operation for moving the capturing area by moving the image capture device,
    wherein the circuitry is configured to generate an image in which the indicator indicating the vertically downward direction is superimposed on the image captured by the image capture device, while the interface is receiving the input.

12. The medical observation system according to claim 8, further comprising:
    a support section that supports the image capture device; and
    a drive controller configured to control the up direction of the image capture device by control of a drive operation of the support section,
    wherein the drive controller causes the up direction of the image capture device to be an opposite direction to the vertically downward direction.

13. The medical observation system according to claim 12, wherein, where the angle that is formed by the up direction of the image capture device and the vertically downward direction exceeds a threshold, the drive controller causes the up direction of the image capture device to be the opposite direction to the vertically downward direction.

14. The medical observation system according to claim 12, comprising
    an interface operable to receive an operation performed by an operator,
    wherein the drive controller causes the up direction of the image capture device to be the opposite direction of the vertically downward direction, according to an instruction that is received from the operator by the interface.

15. The medical observation system according to claim 1, further comprising:
    a controller operable to control the image capture device and to perform image processing on an image that is captured by the image capture device;
    the display device operable to display an image that has undergone the image processing by the controller; and
    a detector operable to detect a position of at least one of the image capture device, the controller, the display device, a surgeon, or an assistant,
    wherein the controller generates an image in which an indicator indicating a position or a direction detected by the detector is superimposed on the image captured by the image capture device.

16. The medical observation system according to claim 15, further comprising
    another detector operable to detect an angle that is formed by the up direction of the image capture device and a vertically downward direction, the up direction of the image capture device corresponding to an up direction of an image that is captured by the image capture device,
    wherein, when the angle that is formed by the up direction of the image capture device and the vertically downward direction exceeds a threshold, an image is generated in which the indicator indicating the position or the direction detected by the detector is superimposed on the image captured by the image capture device.

17. The medical observation system according to claim 15, comprising
    an interface operable to receive an operation performed by an operator,
    wherein the controller generates an image in which the indicator indicating the position or the direction detected by the detector is superimposed on the image captured by the image capture device, according to an instruction that is received from the operator by the interface.

18. The medical observation system according to claim 15, further comprising
    an interface operable to receive an operation for moving the capturing area by moving the image capture device,
    wherein the controller generates an image in which the indicator indicating the position or the direction detected by the detector is superimposed on the image captured by the image capture device, while the interface is receiving the input.

19. A medical observation system comprising:
    an image capture device operable to capture an image of an observation target; and
    a light emitter operable to emit first illumination light in a capturing direction of the image capture device,
    wherein the light emitter radiates second periphery illumination light on the observation target, outside a capturing area that is captured by the image capture device and in a periphery of the capturing area, the second periphery illumination light enabling recognition of a capturing state of the image capture device,
    wherein the capturing state of the image capture device includes a direction of the capturing area, which includes a correspondence relationship between an up direction of the captured image that is displayed on a display device and an up direction of the image capture device, wherein the up direction of the image capture device is perpendicular to a first axis of a first joint portion of a support section, and wherein the correspondence relationship includes an angle between the up direction of the image capture device and a reference direction.

20. The medical observation system according to claim 19, wherein the light emitting emits the second periphery illumination light that enables recognition of a top or bottom portion of the capturing area.

\* \* \* \* \*